United States Patent
Muratoglu et al.

(10) Patent No.: US 8,865,043 B2
(45) Date of Patent: Oct. 21, 2014

(54) METHODS FOR MAKING OXIDATION RESISTANT POLYMERIC MATERIAL

(75) Inventors: Orhun K. Muratoglu, Cambridge, MA (US); Stephen H. Spiegelberg, Winchester, MA (US)

(73) Assignees: The General Hospital Corporation, Boston, MA (US); Cambridge Polymer Group, Inc., Boston, MA (US)

(*) Notice: Subject to any disclaimer, the term of this patent is extended or adjusted under 35 U.S.C. 154(b) by 0 days.

(21) Appl. No.: 13/606,457

(22) Filed: Sep. 7, 2012

(65) Prior Publication Data
US 2013/0062817 A1 Mar. 14, 2013

Related U.S. Application Data

(63) Continuation of application No. 12/904,481, filed on Oct. 14, 2010, now Pat. No. 8,318,065, which is a continuation of application No. 11/568,884, filed as application No. PCT/US2005/016283 on May 10, 2005, now Pat. No. 7,833,452.

(60) Provisional application No. 60/569,624, filed on May 11, 2004.

(51) Int. Cl.
*B29C 35/08* (2006.01)

(52) U.S. Cl.
USPC .......................... 264/235; 264/346

(58) Field of Classification Search
USPC ................................ 264/235, 346
See application file for complete search history.

(56) References Cited

U.S. PATENT DOCUMENTS

| | | | |
|---|---|---|---|
| 3,626,048 A | 12/1971 | Kitazawa et al. | |
| 4,596,728 A | 6/1986 | Yang et al. | |
| 5,411,994 A | 5/1995 | Galli et al. | |
| 5,414,049 A | 5/1995 | Sun et al. | |
| 5,458,826 A * | 10/1995 | Bhuvaneshwar et al. | 264/442 |
| 5,478,906 A | 12/1995 | Howard, Jr. | |
| 5,585,434 A | 12/1996 | DeNicola et al. | |
| 5,753,182 A | 5/1998 | Higgins | |
| 5,797,873 A | 8/1998 | Franz et al. | |
| 5,827,904 A | 10/1998 | Hahn | |

(Continued)

FOREIGN PATENT DOCUMENTS

| | | |
|---|---|---|
| CS | 221403 | 2/1986 |
| EP | 0995450 | 6/2002 |

(Continued)

OTHER PUBLICATIONS

Lederer et al., Alpha-Tocopherol—A Potential Stabilizer for Standard and Crosslinked Ultra-High Molecular Weight Polyethylene (UHMW-PE) Used for Joint Endoprostheses (6th Austrian.

(Continued)

*Primary Examiner* — James Sanders
*Assistant Examiner* — Kimberly A Stewart
(74) *Attorney, Agent, or Firm* — Perkins Coie LLP

(57) ABSTRACT

The present invention relates to methods for making oxidation resistant medical devices that comprise polymeric materials, for example, ultra-high molecular weight polyethylene (UHMWPE). The invention also provides methods of making antioxidant-doped medical implants, for example, doping of medical devices containing cross-linked UHMWPE with vitamin E by diffusion, post-doping annealing, and materials used therein.

21 Claims, 10 Drawing Sheets

(56) References Cited

U.S. PATENT DOCUMENTS

| | | |
|---|---|---|
| 5,879,400 A | 3/1999 | Merrill et al. |
| 6,017,975 A | 1/2000 | Saum et al. |
| 6,184,265 B1 | 2/2001 | Hamilton et al. |
| 6,228,900 B1 | 5/2001 | Shen et al. |
| 6,344,045 B1 | 2/2002 | Lim et al. |
| 6,355,215 B1 | 3/2002 | Poggie et al. |
| 6,448,315 B1 | 9/2002 | Lidgren et al. |
| 6,562,540 B2 | 5/2003 | Saum et al. |
| 6,620,198 B2 | 9/2003 | Burstein et al. |
| 6,641,617 B1 | 11/2003 | Merrill et al. |
| 6,664,346 B2 | 12/2003 | Tsutsumi et al. |
| 6,692,679 B1 | 2/2004 | McNulty et al. |
| 6,818,172 B2 | 11/2004 | King et al. |
| 7,431,874 B2 | 10/2008 | Muratoglu et al. |
| 7,833,452 B2 | 11/2010 | Muratoglu et al. |
| 7,906,064 B2 | 3/2011 | Muratoglu et al. |
| 8,318,065 B2 | 11/2012 | Muratoglu et al. |
| 2002/0055784 A1 | 5/2002 | Burstein et al. |
| 2003/0208278 A1 | 11/2003 | Richard et al. |
| 2003/0212161 A1 | 11/2003 | McKellop et al. |
| 2004/0156879 A1 | 8/2004 | Muratoglu et al. |
| 2005/0194722 A1 | 9/2005 | Muratoglu et al. |
| 2005/0194723 A1 | 9/2005 | Muratoglu et al. |
| 2006/0223905 A1 | 10/2006 | Mimnaugh et al. |
| 2007/0114702 A1 | 5/2007 | Muratoglu et al. |
| 2008/0067724 A1 | 3/2008 | Muratoglu et al. |
| 2008/0090934 A1 * | 4/2008 | Muratoglu et al. ........... 522/161 |
| 2008/0119582 A1 | 5/2008 | Muratoglu et al. |
| 2011/0004315 A1 | 1/2011 | Muratoglu et al. |
| 2011/0039969 A1 | 2/2011 | Muratoglu et al. |
| 2012/0215321 A1 | 8/2012 | Muratoglu et al. |

FOREIGN PATENT DOCUMENTS

| | | |
|---|---|---|
| JP | 11-239611 | 9/1999 |
| WO | WO90/06139 | 6/1990 |
| WO | WO97/29793 | 8/1997 |
| WO | WO01/05337 | 1/2001 |
| WO | WO01/80778 | 11/2001 |
| WO | WO02/26464 | 4/2002 |
| WO | WO 03/059200 | 7/2003 |
| WO | WO2004/064618 | 8/2004 |
| WO | WO2005/110276 | 11/2005 |

OTHER PUBLICATIONS

Lee et al., Macromolecular Research 12(1): 112-118 (2004).
Mori et al., Mechanical Behavior of UHMWPE When Mixed with Vitamin E (47$^{th}$ Annual Meeting, Orthopaedic Research Society, San Francisco, CA (Feb. 25-28, 2001).
Muratoglu et al., Biomaterials 20: 1463-1470 (1999).
Muratoglu et al., Clinical Orthopaedics and Related Research 417:253-262 (2003).
Parth et al., Journal of Materials Science: Materials in Medicine 13: 917-921 (2002).
Wolf et al., Journal of Materials Science: Materials in Medicine 13: 701-705 (2002).
Appleby et al., Journal of Materials Science 29: 227-231 (1994).

* cited by examiner

US 8,865,043 B2

METHODS FOR MAKING OXIDATION RESISTANT POLYMERIC MATERIAL

This application is a continuation of U.S. application Ser. No. 12/904,481 filed Oct. 14, 2010 now U.S. Pat. No. 8,318, 065, which is a continuation of U.S. application Ser. No. 11/568,884 filed Feb. 9, 2007, now U.S. Pat. No. 7,833,452, which is a 371 of PCT/US2005/016283 filed May 10, 2005, which claims the benefit of U.S. Provisional Application No. 60/569,624 filed May 11, 2004. The entire contents of the above-identified applications are hereby incorporated by reference.

FIELD OF THE INVENTION

The present invention relates to methods for making oxidation resistant medical devices that comprise polymeric materials. Methods of doping polyethylene with an antioxidant (for example, vitamin E) post-doping annealing, and materials used therewith also are provided.

BACKGROUND OF THE INVENTION

Oxidation resistant cross-linked polymeric material, such as ultra-high molecular weight polyethylene (UHMWPE), is desired in medical devices because it significantly increases the wear resistance of the devices. The preferred method of crosslinking is by exposing the UHMWPE to ionizing radiation. However, ionizing radiation, in addition to crosslinking, also will generate residual free radicals, which are the precursors of oxidation-induced embrittlement. Melting during or after irradiation has been used to eliminate the crystals and allow the residual free radicals to recombine with each other. The irradiation with subsequent melting is used to reduce the potential for oxidation secondary to the residual free radicals. However, such melting reduces the crystallinity of UHMWPE, which, in turn, decreases the yield strength, ultimate tensile strength, modulus, and fatigue strength of UHMWPE. For certain applications that require high fatigue resistance, such highly crosslinked UHMWPE (that is irradiated and melted) may not be suitable; because, fatigue failure in the long term may compromise the performance of the medical device. Therefore, there is a need to either eliminate the residual free radicals or the oxidative effect of residual free radicals without melting. Such a method would preserve the crystallinity of the irradiated UHMWPE and also preserve the mechanical properties and fatigue resistance.

It is generally known that mixing of polyethylene powder with an antioxidant prior to consolidation may improve the oxidation resistance of the polyethylene material. Antioxidants, such as vitamin E and β-carotene, have been mixed with UHMWPE powder or particles by several investigators (see, Mori et al. p. 1017, *Hand-out at the 47th Annual Meeting, Orthopaedic Res Soc*, Feb. 25-28, 2001, San Francisco, Calif.; McKellop et al. WO 01/80778; Schaffner et al. EP 0 995 450; Hahn D. U.S. Pat. No. 5,827,904; Lidgren et al. U.S. Pat. No. 6,448,315), in attempts to improve wear resistance. Mori et al. also described that irradiation does not decrease the oxidation resistance of antioxidant-doped polyethylene. The investigators (see, McKellop et al. WO 01/80778; Schaffner et al. EP 0 995 450; Hahn D. U.S. Pat. No. 5,827, 904; Lidgren et al. U.S. Pat. No. 6,448,315) described mixing polyethylene powder with antioxidants, followed by consolidating the antioxidant-powder mix to obtain oxidation resistant polyethylene. Mixing of the resin powder, flakes, or particles with vitamin E and consolidation thereafter result in changes in color of polymeric material to yellow (see for example, U.S. Pat. No. 6,448,315). In addition, the addition of the antioxidant to the UHMWPE prior to irradiation can inhibit crosslinking of the UHMWPE during irradiation. However, crosslinking is needed to increase the wear resistance of the polymer. Therefore, it would be preferable to have a medical implant, or any polymeric component thereof, doped with an antioxidant and subsequent annealing in its consolidated solid form, such as feed-stock, machined components, or molded components.

SUMMARY OF THE INVENTION

The present invention relates generally to methods of making oxidation resistant medical devices that comprise one or more polymeric materials, as well as such materials made thereby. More specifically, the invention relates to methods of manufacturing antioxidant doped medical devices containing cross-linked polyethylene, for example, cross-linked ultra-high molecular weight polyethylene (UHMWPE), and materials used therein, as well as such materials made thereby. More specifically, the invention relates to methods of manufacturing antioxidant-doped, non-oxidizing medical device containing cross-linked polyethylene with residual free radicals, for example, irradiated ultra-high molecular weight polyethylene (UHMWPE) and materials used therein, and materials made thereby.

In one aspect, the invention provides methods of making cross-linked polymeric material comprising the steps of: a) providing consolidated and cross-linked polymeric material that has been irradiated with ionizing radiation; b) doping the consolidated and cross-linked polymeric material with an antioxidant by diffusion; and c) annealing the antioxidant-doped cross-linked polymeric material in liquid or gaseous environment and under various temperature and pressure conditions, for example, in boiling water under atmospheric pressure. Cross-linked polymeric materials obtainable by these methods also are provided.

In another aspect, the invention provides methods of making cross-linked polymeric material comprising the steps of: a) providing consolidated and cross-linked polymeric material that has been irradiated with ionizing radiation; b) doping the consolidated and cross-linked polymeric material with an antioxidant by diffusion; c) annealing the antioxidant-doped cross-linked polymeric material in liquid or gaseous environment and under various temperature and pressure conditions, for example, in boiling water under atmospheric pressure; and d) heating the consolidated and cross-linked polymeric material to a temperature below the melting point of the consolidated and cross-linked polymeric material. Cross-linked polymeric materials obtainable by these methods also are provided.

In another aspect, the invention provides methods of making cross-linked polymeric material, wherein the cross-linked polymeric material is soaked in a solution, of about 50% by weight, of an antioxidant in an alcohol, such as ethanol, wherein the cross-linked polymeric material is diffused with the antioxidant in a supercritical fluid, such as $CO_2$. Cross-linked polymeric materials obtainable by these methods also are provided.

In another aspect, the invention provides methods of making cross-linked polymeric material comprising the steps of: a) placing a consolidated and cross-linked polymeric material in a pressure chamber; b) filling the chamber with an antioxidant, either in a neat form (about 100%) or in a solution such as a 50% mixture of the antioxidant and alcohol, such as ethanol; c) pressurizing the chamber to enhance diffusion of the antioxidant into the consolidated and cross-linked polymeric material; and d) annealing the antioxidant-doped cross-linked polymeric material in liquid or gaseous environment and under various temperature and pressure conditions, for example, in boiling water under atmospheric pressure. Cross-linked polymeric materials obtainable by these methods also are provided.

In another aspect, the invention provides methods of making cross-linked polymeric material comprising the steps of a) doping the consolidated polymeric material with an antioxidant by diffusion; and b) annealing the antioxidant-doped polymeric material in liquid or gaseous environment and under various temperature and pressure conditions, for example, in boiling water under atmospheric pressure; c) irradiating the consolidated polymeric material with ionizing radiation, thereby forming a consolidated and cross-linked polymeric material; and d) annealing the consolidated and cross-linked polymeric material at a temperature below or above melt of the consolidated and cross-linked polymeric material. Cross-linked polymeric materials obtainable by these methods also are provided.

According to another aspect, the invention provides methods of making cross-linked polymeric material, comprising the steps of: a) consolidating a polymeric material; b) irradiating the polymeric material with ionizing radiation, thereby forming a consolidated and cross-linked polymeric material; c) doping the consolidated and cross-linked polymeric material with an antioxidant by diffusion; d) annealing the antioxidant-doped cross-linked polymeric material in liquid or gaseous environment and under various temperature and pressure conditions, for example, in boiling water under atmospheric pressure; and e) heating the consolidated and cross-linked polymeric material at a temperature below the melting point of the consolidated and cross-linked polymeric material. Cross-linked polymeric materials obtainable by these methods also are provided.

In another aspect, the invention provides methods of making a medical implant comprising: a) providing a polymeric material; b) consolidating the polymeric material; c) irradiating the consolidated polymeric material with ionizing radiation, thereby forming a consolidated and cross-linked polymeric material; d) machining the consolidated and cross-linked polymeric material, thereby forming a medical implant; e) doping the medical implant with an antioxidant by diffusion, thereby forming an antioxidant-doped cross-linked medical implant; and f) annealing the antioxidant-doped cross-linked medical implant in liquid or gaseous environment and under various temperature and pressure conditions, for example, in boiling water under atmospheric pressure. Medical implants obtainable by these methods also are provided.

In another aspect, the invention provides methods of making a medical implant comprising: a) providing a consolidated polymeric material; b) irradiating the consolidated polymeric material with ionizing radiation, thereby forming a consolidated and cross-linked polymeric material; c) machining the consolidated and cross-linked polymeric material, thereby forming a medical implant; d) doping the medical implant with an antioxidant by diffusion, thereby forming an antioxidant-doped cross-linked medical implant; and e) annealing the antioxidant-doped cross-linked medical implant in liquid or gaseous environment and under various temperature and pressure conditions, for example, in boiling water under atmospheric pressure. Medical implants obtainable by these methods also are provided.

In another aspect, the invention provides methods of making a medical implant containing antioxidant-doped cross-linked polymeric material comprising: a) irradiating a consolidated polymeric material with ionizing radiation, thereby forming a cross-linked polymeric material; b) machining the consolidated and cross-linked polymeric material, thereby forming a medical implant; c) doping the medical implant with an antioxidant by diffusion; and d) annealing the antioxidant-doped cross-linked medical implant in liquid or gaseous environment and under various temperature and pressure conditions, for example, in boiling water under atmospheric pressure. Medical implants obtainable by these methods also are provided.

In another aspect, the invention provides methods of making a medical implant containing antioxidant-doped cross-linked polymeric material comprising: a) machining a consolidated polymeric material, thereby forming a medical implant; b) doping the medical implant with an antioxidant by diffusion; c) annealing the antioxidant-doped medical implant in liquid or gaseous environment and under various temperature and pressure conditions, for example, in boiling water under atmospheric pressure; and d) irradiating the medical implant, thereby forming a medical implant containing cross-linked polymeric material. Medical implants obtainable by these methods also are provided.

In another aspect, the invention provides methods of making a medical implant containing polymeric material comprising: a) irradiating the polymeric material with ionizing radiation, thereby forming a cross-linked polymeric material; b) doping the cross-linked polymeric material with an antioxidant by diffusion, wherein the cross-linked polymeric material is annealed at a temperature below the melt or above the melt of the consolidated and cross-linked polymeric material; and c) annealing the antioxidant-doped cross-linked polymeric material in liquid or gaseous environment and under various temperature and pressure conditions, for example, in boiling water under atmospheric pressure. Medical implants obtainable by these methods also are provided.

In another aspect, the invention provides methods of making a medical implant containing cross-linked polymeric material comprising: a) compression molding of polymeric material to another piece, thereby forming an interface and an interlocked hybrid material; b) irradiating the interlocked hybrid material by ionizing radiation, thereby forming a cross-linked and interlocked hybrid material; c) doping the cross-linked and interlocked hybrid material with an antioxidant by diffusion; and d) annealing the antioxidant-doped cross-linked interlocked hybrid in liquid or gaseous environment and under various temperature and pressure conditions, for example, in boiling water under atmospheric pressure. Medical implants containing cross-linked polymeric materials that are obtainable by these methods also are provided.

In another aspect, the invention provides methods of making a medical implant containing cross-linked polymeric material comprising: a) compression molding of polymeric material to another piece, thereby forming an interface and an interlocked hybrid material; b) doping the interlocked hybrid material with an antioxidant by diffusion; c) annealing the antioxidant-doped interlocked hybrid in liquid or gaseous environment and under various temperature and pressure conditions, for example, in boiling water under atmospheric pressure; and d) irradiating the interlocked hybrid material by ionizing radiation, thereby forming a cross-linked and interlocked hybrid material. Medical implants containing cross-linked polymeric materials that are obtainable by these methods also are provided.

In another aspect, the invention provides methods of making a sterile medical implant containing cross-linked polymeric material comprising: a) direct compression molding a polymeric material, thereby forming a medical implant; b)

irradiating the medical implant to crosslink the polymeric material; c) doping the irradiated medical implant with an antioxidant by diffusion; d) annealing the antioxidant-doped cross-linked medical implant in liquid or gaseous environment and under various temperature and pressure conditions, for example, in boiling water under atmospheric pressure; e) packaging the irradiated and antioxidant-doped medical implant; and f) sterilizing the packaged irradiated and antioxidant-doped medical implant by ionizing radiation or gas sterilization, thereby forming a cross-linked and sterile medical implant. Medical implants containing cross-linked polymeric materials that are obtainable by these methods also are provided.

In another aspect, the invention provides methods of making a sterile medical implant containing antioxidant doped cross-linked polymeric material comprising: a) machining a consolidated polymeric material, thereby forming a medical implant; b) irradiating the medical implant, thereby forming a medical implant containing cross-linked polymeric material; c) doping the medical implant with an antioxidant by diffusion; d) annealing the antioxidant-doped cross-linked medical implant in liquid or gaseous environment and under various temperature and pressure conditions, for example, in boiling water under atmospheric pressure; e) packaging the irradiated and antioxidant-doped medical implant; and f) sterilizing the packaged medical implant by ionizing radiation or gas sterilization, thereby forming a cross-linked and sterile medical implant. Medical implants obtainable by these methods also are provided.

In another aspect, the invention provides methods of making a medical implant containing cross-linked polymeric material comprising: a) doping a polymeric material with an antioxidant by diffusion; b) annealing the antioxidant-doped polymeric material in liquid or gaseous environment and under various temperature and pressure conditions, for example, in boiling water under atmospheric pressure; c) compression molding of the polymeric material to another piece, thereby forming an interface and an interlocked hybrid material; and d) irradiating the interlocked hybrid material by ionizing radiation, thereby forming a cross-linked and interlocked hybrid material. Medical implants containing cross-linked polymeric materials that are obtainable by these methods also are provided.

In another aspect, the invention provides methods of making a medical implant containing cross-linked polymeric material comprising: a) direct compression molding of the polymeric material, thereby forming a medical implant; b) irradiating the medical implant by ionizing radiation, thereby forming a consolidated and cross-linked medical implant; c) doping the consolidated and cross-linked medical implant with an antioxidant by diffusion; and d) annealing the antioxidant-doped cross-linked medical implant in liquid or gaseous environment and under various temperature and pressure conditions, for example, in boiling water under atmospheric pressure. Medical implants containing cross-linked polymeric materials that are obtainable by these methods also are provided.

In another aspect, the invention provides methods of making a medical implant containing antioxidant-doped cross-linked polymeric material comprising: a) machining a consolidated polymeric material, thereby forming a medical implant; b) irradiating the medical implant, thereby forming a medical implant containing cross-linked polymeric material; c) doping the medical implant with an antioxidant by diffusion; and d) annealing the antioxidant-doped cross-linked medical implant in liquid or gaseous environment and under various temperature and pressure conditions, for example, in boiling water under atmospheric pressure. Medical implants containing antioxidant-doped cross-linked polymeric materials that are obtainable by these methods also are provided.

In another aspect, the invention provides methods of making a medical implant containing cross-linked polymeric material comprising: a) direct compression molding polymeric material, thereby forming a medical implant; b) doping the medical implant with an antioxidant by diffusion; c) annealing the antioxidant-doped medical implant in liquid or gaseous environment and under various temperature and pressure conditions, for example, in boiling water under atmospheric pressure; d) packaging the medical implant; and e) irradiating the packaged medical implant by ionizing radiation, thereby forming a consolidated and cross-linked and sterile medical implant. Medical implants containing cross-linked polymeric materials that are obtainable by these methods also are provided.

In another aspect, the invention provides methods of making a medical implant containing cross-linked polymeric material comprising: a) machining a consolidated polymeric material, thereby forming a medical implant; b) doping the medical implant with an antioxidant by diffusion; c) annealing the antioxidant-doped medical implant in liquid or gaseous environment and under various temperature and pressure conditions, for example, in boiling water under atmospheric pressure; d) packaging the medical implant; and e) irradiating the packaged medical implant by ionizing radiation, thereby forming a consolidated and cross-linked and sterile medical implant. Medical implants containing cross-linked polymeric materials that are obtainable by these methods also are provided.

In another aspect, the invention provides methods of making cross-linked polymeric material comprising the steps of: a) placing a consolidated and cross-linked polymeric material in a pressure chamber; b) filling the chamber with an antioxidant; c) pressurizing the chamber to enhance diffusion of the antioxidant into the consolidated and cross-linked polymeric material; and d) annealing the antioxidant-doped cross-linked polymeric material in liquid or gaseous environment and under various temperature and pressure conditions, for example, in boiling water under atmospheric pressure. Medical implants containing antioxidant-doped cross-linked polymeric materials that are obtainable by these methods also are provided.

In another aspect, the invention provides methods of making medical devices containing cross-linked polymeric material comprising: a) irradiating a manufactured medical device consisting of consolidated polymeric material with ionizing radiation, thereby forming a consolidated and cross-linked polymeric material; b) doping the consolidated and cross-linked polymeric material with an antioxidant by diffusion, thereby forming an antioxidant-doped consolidated and cross-linked polymeric material; and c) annealing the antioxidant-doped cross-linked polymeric material in liquid or gaseous environment and under various temperature and pressure conditions, for example, in boiling water under atmospheric pressure. Medical devices containing cross-linked polymeric materials that are obtainable by these methods also are provided.

In another aspect, the invention provides methods of making a packaging for medical devices that is resistant to oxidation, when subjected to either sterilization or crosslinking doses of ionizing radiation, comprising: a) doping the packaging material with an antioxidant by diffusion; b) annealing the antioxidant-doped packaging material in liquid or gaseous environment and under various temperature and pressure conditions, for example, in boiling water under atmospheric pressure; c) inserting a medical device in the packaging material; d) sealing the packaging material containing the medical device, thereby forming a packaged medical device; and d) irradiating the packaged medical device with ionizing radiation or gas sterilization. Medical devices obtainable by these methods also are provided.

In another aspect, the invention provides methods of making a packaging for pharmaceutical compounds that is resistant to oxidation, when subjected to either sterilization or crosslinking doses of ionizing radiation, comprising: a) doping the packaging material with an antioxidant by diffusion; b) annealing the antioxidant-doped packaging material in liquid or gaseous environment and under various temperature and pressure conditions, for example, in boiling water under atmospheric pressure; c) inserting a pharmaceutical compound in the packaging material; d) sealing the packaging material containing the pharmaceutical compound, thereby forming a packaged pharmaceutical compound; and e) irradiating the packaged pharmaceutical compound with ionizing radiation or gas sterilization. Packaging materials obtainable by these methods also are provided.

Yet in another aspect, the invention provides methods of making a medical implant containing cross-linked polymeric material, wherein the implant comprises medical devices, including acetabular liner, shoulder glenoid, patellar component, finger joint component, ankle joint component, elbow joint component, wrist joint component, toe joint component, bipolar hip replacements, tibial knee insert, tibial knee inserts with reinforcing metallic and polyethylene posts, intervertebral discs, heart valves, tendons, stents, and vascular grafts, wherein the polymeric material is polymeric resin powder, polymeric flakes, polymeric particles, or the like, or a mixture thereof. Medical implants containing cross-linked polymeric materials that are obtainable by these methods also are provided.

Yet in another aspect, the invention provides methods of making medical implants, including non-permanent implants, containing cross-linked polymeric material, wherein the implant comprises medical device, including balloon catheters, sutures, tubing, and intravenous tubing, wherein the polymeric material is polymeric resin powder, polymeric flakes, polymeric particles, or the like, or a mixture thereof. As described herein, the polymeric balloons, for example, polyether-block co-polyamide polymer (PeBAX®), Nylon, and polyethylene terephthalate (PET) balloons are doped with vitamin E and irradiated before, during, or after doping. Medical implants obtainable by these methods also are provided.

Yet in another aspect, the invention provides methods of making a packaging for a medical device, wherein the packaging is resistant to oxidation when subjected to sterilization with ionizing radiation or gas sterilization. The packaging include barrier materials, for example, blow-molded blister packs, heat-shrinkable packaging, thermally-sealed packaging, or the like or a mixture thereof. Packaging materials for a medical devices obtainable by these methods also are provided.

In another aspect, the invention provides methods of making a medical implant containing cross-linked polymeric material comprising: a) doping the consolidated polymeric material with an antioxidant by diffusion; b) annealing the antioxidant-doped polymeric material in liquid or gaseous environment and under various temperature and pressure conditions, for example, in boiling water under atmospheric pressure; and c) irradiating the polymeric material with ionizing radiation, thereby forming a consolidated and cross-linked polymeric material. Medical implants containing cross-linked polymeric materials obtainable by these methods also are provided.

In one aspect, antioxidant-doped medical implants are packaged and sterilized by ionizing radiation or gas sterilization to obtain sterile and cross-linked medical implants.

In another aspect, the polymeric material of the instant invention is a polymeric resin powder, polymeric flakes, polymeric particles, or the like, or a mixture thereof, wherein the irradiation can be carried out in an atmosphere containing between about 1% and about 22% oxygen, wherein the radiation dose is between about 25 kGy and about 1000 kGy.

In another aspect, the polymeric material of the instant invention is polymeric resin powder, polymeric flakes, polymeric particles, or the like, or a mixture thereof, wherein the polymeric material is irradiated after consolidation in an inert atmosphere containing a gas, for example, nitrogen, argon, helium, neon, or the like, or a combination thereof, wherein the radiation dose is between about 25 kGy and about 1000 kGy.

In another aspect, the polymeric material of the instant invention is consolidated polymeric material, where the consolidation can be carried out by compression molding to form a slab from which a medical device is machined.

In another aspect, the polymeric material of the instant invention is consolidated polymeric material, where the consolidation can be carried out by direct compression molding to form a finished medical device.

Yet in another aspect, the polymeric material of the instant invention is consolidated polymeric material, where the consolidation can be carried out by compression molding to another piece to form an interface and an interlocked hybrid material.

Still in another aspect, the invention provides methods of making a medical implant containing cross-linked polymeric material comprising: a) compression molding of polymeric material to another piece, thereby forming an interface and an interlocked hybrid material; b) irradiating the interlocked hybrid material by ionizing radiation, thereby forming a cross-linked and interlocked hybrid material; c) doping the cross-linked and interlocked hybrid material with an antioxidant by diffusion; and d) annealing the antioxidant-doped cross-linked and interlocked hybrid material in liquid or gaseous environment and under various temperature and pressure conditions, for example, in boiling water under atmospheric pressure. Medical implants containing cross-linked polymeric materials that are obtainable by these methods also are provided.

According to one aspect, the invention provides methods of making a medical implant containing cross-linked polymeric material comprising compression molding of polymeric material to another piece, such as a metallic or a non metallic piece, for example, a metal, a ceramic, or a polymer, thereby forming an interface and an interlocked hybrid material, wherein the interface is a metal-polymer or a metal-ceramic interface.

Yet according to another aspect, the invention provides methods of making a medical implant containing cross-linked polymeric material comprising: a) compression molding of polymeric material to another piece, thereby forming an interface and an interlocked hybrid material; b) annealing the antioxidant-doped interlocked hybrid material in liquid or gaseous environment and under various temperature and pressure conditions, for example, in boiling water under atmospheric pressure; c) doping the interlocked hybrid material with an antioxidant, for example, an α-tocopherol, such as vitamin E, by diffusion; and d) irradiating the interlocked hybrid material by ionizing radiation, thereby forming a cross-linked and interlocked hybrid material. Medical implants containing cross-linked polymeric materials that are obtainable by these methods also are provided.

Another aspect of the invention provides methods of making a medical implant containing cross-linked polymeric material comprising: a) compression molding a polymeric material, thereby forming a medical implant; b) irradiating the medical implant to crosslink the polymeric material; c) annealing the antioxidant-doped cross-linked medical implant in liquid or gaseous environment and under various temperature and pressure conditions, for example, in boiling water under atmospheric pressure; d) doping the irradiated medical implant with an antioxidant by diffusion; e) packaging the irradiated and antioxidant-doped medical implant; and sterilizing the packaged irradiated and antioxidant-doped medical implant by ionizing radiation or gas sterilization, thereby forming a cross-linked and sterile medical implant. Medical implants obtainable by these methods also are provided.

Yet in another aspect, the invention provides methods of making a medical implant containing cross-linked polymeric material comprising: a) machining a consolidated polymeric material, thereby forming a medical implant; b) irradiating the medical implant to crosslink the polymeric material; c) doping the irradiated medical implant with an antioxidant by diffusion; d) annealing the antioxidant-doped cross-linked medical implant in liquid or gaseous environment and under various temperature and pressure conditions, for example, in boiling water under atmospheric pressure; e) packaging the irradiated and antioxidant-doped medical implant; and f) sterilizing the packaged irradiated and antioxidant-doped medical implant by ionizing radiation or gas sterilization, thereby forming a cross-linked and sterile medical implant. Medical implants obtainable by these methods also are provided.

According to another aspect, the invention provides methods of making a medical implant containing cross-linked polymeric material comprising: a) compression molding of polymeric material to another piece, thereby forming an interface and an interlocked hybrid material; b) doping the interlocked hybrid material with an antioxidant by diffusion; c) annealing the antioxidant-doped interlocked hybrid material in liquid or gaseous environment and under various temperature and pressure conditions, for example, in boiling water under atmospheric pressure; and d) irradiating the interlocked hybrid material by ionizing radiation, thereby forming a cross-linked and interlocked hybrid material. Medical implants containing cross-linked polymeric material obtainable by these methods also are provided.

In another aspect, the invention provides methods of making a medical implant containing cross-linked polymeric material comprising: a) direct compression molding of the polymeric material, thereby forming a medical implant; b) irradiating the medical implant by ionizing radiation, thereby forming a consolidated and cross-linked medical implant; c) doping the consolidated and cross-linked medical implant with an antioxidant by diffusion; and d) annealing the antioxidant-doped cross-linked medical implant in liquid or gaseous environment and under various temperature and pressure conditions, for example, in boiling water under atmospheric pressure. Medical implants containing cross-linked polymeric materials obtainable by these methods also are provided.

Yet in another aspect, the invention provides methods of making a medical implant containing cross-linked polymeric material comprising: a) machining a consolidated polymeric material, thereby forming a medical implant; b) irradiating the medical implant by ionizing radiation, thereby forming a consolidated and cross-linked medical implant; c) doping the consolidated and cross-linked medical implant an antioxidant by diffusion; and d) annealing the antioxidant-doped cross-linked medical implant in liquid or gaseous environment and under various temperature and pressure conditions, for example, in boiling water under atmospheric pressure. Medical implants obtainable by these methods also are provided.

In another aspect, the invention provides methods of making a medical implant comprising: a) providing a polymeric material; b) consolidating the polymeric material; c) doping the consolidated polymeric material with an antioxidant by diffusion; d) annealing the antioxidant-doped polymeric material in liquid or gaseous environment and under various temperature and pressure conditions, for example, in boiling water under atmospheric pressure; e) irradiating the antioxidant doped polymeric material by ionizing radiation, thereby forming an antioxidant doped cross-linked polymeric material; and f) machining the cross-linked polymeric material, thereby forming an antioxidant doped cross-linked medical implant. Medical implants obtainable by these methods also are provided.

In another aspect, the invention provides methods of making a medical implant comprising: a) providing a consolidated polymeric material; b) doping the consolidated polymeric material with an antioxidant by diffusion; c) annealing the antioxidant-doped polymeric material in liquid or gaseous environment and under various temperature and pressure conditions, for example, in boiling water under atmospheric pressure; d) irradiating the antioxidant doped polymeric material by ionizing radiation, thereby forming an antioxidant doped cross-linked polymeric material; and e) machining the cross-linked polymeric material, thereby forming an antioxidant doped cross-linked medical implant. Medical implants obtainable by these methods also are provided.

In another aspect, the invention provides methods of making a medical implant comprising: a) providing a polymeric material; b) consolidating the polymeric material; c) doping the consolidated polymeric material with an antioxidant by diffusion; d) annealing the antioxidant-doped polymeric material in liquid or gaseous environment and under various temperature and pressure conditions, for example, in boiling water under atmospheric pressure; e) machining the antioxidant doped polymeric material, thereby forming an antioxidant doped polymeric material; and f) irradiating the antioxidant doped cross-linked polymeric material by ionizing radiation, thereby forming an antioxidant doped cross-linked medical implant.

In another aspect, the invention provides methods of making a medical implant comprising: a) providing a consolidated polymeric material; b) doping the consolidated polymeric material with an antioxidant by diffusion; c) annealing the antioxidant-doped polymeric material in liquid or gaseous environment and under various temperature and pressure conditions, for example, in boiling water under atmospheric pressure; d) machining the antioxidant doped polymeric material, thereby forming an antioxidant doped polymeric material; and e) irradiating the antioxidant doped cross-linked polymeric material by ionizing radiation, thereby forming an antioxidant doped cross-linked medical implant.

In another aspect, the invention provides methods of making a medical implant containing cross-linked polymeric material comprising: a) direct compression molding polymeric material, thereby forming a medical implant; b) doping the medical implant an antioxidant by diffusion; c) packaging the medical implant; d) annealing the antioxidant-doped medical implant in liquid or gaseous environment and under various temperature and pressure conditions, for example, in boiling water under atmospheric pressure; and e) irradiating the packaged medical implant by ionizing radiation, thereby forming a consolidated and cross-linked and sterile medical implant.

In another aspect, the invention provides methods of making a medical implant comprising: a) providing a polymeric material; b) consolidating the polymeric material; c) machining the consolidated polymeric material, thereby forming a medical implant; d) doping the medical implant with an antioxidant by diffusion, thereby forming an antioxidant-doped medical implant; e) annealing the antioxidant-doped medical implant in liquid or gaseous environment and under various temperature and pressure conditions, for example, in boiling water under atmospheric pressure; f) packaging the medical implant; and g) irradiating the packaged medical implant by ionizing radiation, thereby forming an antioxidant doped cross-linked and sterile medical implant.

Yet in another aspect, the invention provides methods of making a medical implant comprising: a) providing a consolidated polymeric material; b) machining the consolidated polymeric material, thereby forming a medical implant; c) doping the medical implant with an antioxidant by diffusion, thereby forming an antioxidant doped medical implant; d) annealing the antioxidant-doped medical implant in liquid or gaseous environment and under various temperature and pressure conditions, for example, in boiling water under atmospheric pressure; e) packaging the medical implant; and f) irradiating the packaged medical implant by ionizing radiation, thereby forming an antioxidant doped cross-linked and sterile medical implant.

In another aspect, the invention provides methods of making a medical implant comprising: a) providing a polymeric material; b) consolidating the polymeric material; c) doping the consolidated polymeric material with an antioxidant by diffusion, thereby forming an antioxidant doped polymeric material; d) annealing the antioxidant-doped polymeric material in liquid or gaseous environment and under various temperature and pressure conditions, for example, in boiling water under atmospheric pressure; e) machining the antioxidant-doped polymeric material, thereby forming a medical implant; f) packaging the medical implant; and g) irradiating the packaged medical implant by ionizing radiation, thereby forming an antioxidant doped cross-linked and sterile medical implant.

Yet in another aspect, the invention provides methods of making a medical implant comprising: a) providing a consolidated polymeric material; b) doping the consolidated polymeric material with an antioxidant by diffusion, thereby forming an antioxidant-doped polymeric material; c) annealing the antioxidant-doped polymeric material in liquid or gaseous environment and under various temperature and pressure conditions, for example, in boiling water under atmospheric pressure; d) machining the antioxidant-doped polymeric material, thereby forming a medical implant; e) packaging the medical implant; and f) irradiating the packaged medical implant by ionizing radiation, thereby forming an antioxidant doped cross-linked and sterile medical implant.

In another aspect, the invention provides methods of making a sterile medical implant containing antioxidant doped cross-linked polymeric material comprising: a) irradiating a consolidated polymeric material, thereby forming a cross-linked polymeric material; b) machining the consolidated and cross-linked polymeric material, thereby forming a medical implant; c) doping the medical implant with an antioxidant by diffusion; d) annealing the antioxidant-doped cross-linked medical implant in liquid or gaseous environment and under various temperature and pressure conditions, for example, in boiling water under atmospheric pressure; e) packaging the irradiated and antioxidant-doped medical implant; and f) sterilizing the packaged medical implant by ionizing radiation or gas sterilization, thereby forming a cross-linked and sterile medical implant.

In another aspect, the invention provides methods of making a sterile medical implant containing antioxidant doped cross-linked polymeric material comprising: a) doping a polymeric material with an antioxidant; b) annealing the antioxidant-doped polymeric material in liquid or gaseous environment and under various temperature and pressure conditions, for example, in boiling water under atmospheric pressure; c) consolidating the antioxidant-doped polymeric material; d) machining the consolidated antioxidant-doped polymeric material, thereby forming an antioxidant-doped medical implant; e) irradiating the medical implant, thereby forming a medical implant containing antioxidant-doped cross-linked polymeric material; f) packaging the antioxidant-doped cross-linked medical implant; and g) sterilizing the packaged medical implant by ionizing radiation or gas sterilization, thereby forming a cross-linked and sterile medical implant.

In another aspect, the invention provides methods of making a sterile medical implant containing antioxidant doped cross-linked polymeric material comprising: a) doping a polymeric material with an antioxidant; b) annealing the antioxidant-doped polymeric material in liquid or gaseous environment and under various temperature and pressure conditions, for example, in boiling water under atmospheric pressure; c) consolidating the antioxidant-doped polymeric material; d) irradiating the consolidated polymeric material, thereby forming an antioxidant-doped cross-linked polymeric material; e) machining the consolidated and cross-linked polymeric material, thereby forming a medical implant containing an antioxidant-doped cross-linked polymeric material; f) packaging the antioxidant-doped cross-linked medical implant; and g) sterilizing the packaged medical implant by ionizing radiation or gas sterilization, thereby forming a cross-linked and sterile medical implant.

In another aspect, the invention provides methods of making a medical implant containing cross-linked polymeric material comprising: a) doping a polymeric material with an antioxidant by diffusion; b) annealing the antioxidant-doped polymeric material in liquid or gaseous environment and under various temperature and pressure conditions, for example, in boiling water under atmospheric pressure; c) irradiating the antioxidant-doped polymeric material by ionizing radiation, thereby forming a cross-linked antioxidant-doped polymeric material; and d) compression molding of the cross-linked antioxidant-doped polymeric material to another piece, thereby forming a cross-linked and interlocked hybrid material.

In another aspect, the invention provides methods of making a medical implant containing cross-linked polymeric material comprising: a) irradiating a consolidated polymeric material by ionizing radiation, thereby forming a consolidated and cross-linked polymeric material; b) direct compression molding of the polymeric material, thereby forming a consolidated and cross-linked medical implant; c) doping the consolidated and cross-linked medical implant with an antioxidant by diffusion; and d) annealing the antioxidant-doped cross-linked medical implant in liquid or gaseous environment and under various temperature and pressure conditions, for example, in boiling water under atmospheric pressure.

In another aspect, the invention provides methods of making a medical implant containing antioxidant doped cross-linked polymeric material comprising: a) doping a polymeric material with an antioxidant; b) annealing the antioxidant-doped polymeric material in liquid or gaseous environment and under various temperature and pressure conditions, for example, in boiling water under atmospheric pressure; c) consolidating the antioxidant-doped polymeric material; d) machining the consolidated antioxidant-doped polymeric material, thereby forming an antioxidant-doped medical implant; and e) irradiating the medical implant, thereby forming a medical implant containing antioxidant-doped cross-linked polymeric material.

In another aspect, the invention provides methods of making a medical implant containing antioxidant doped cross-linked polymeric material comprising: a) doping a polymeric material with an antioxidant; b) annealing the antioxidant-doped polymeric material in liquid or gaseous environment and under various temperature and pressure conditions, for example, in boiling water under atmospheric pressure; c) consolidating the antioxidant-doped polymeric material; d) irradiating the consolidated polymeric material, thereby forming an antioxidant-doped cross-linked polymeric material; and e) machining the consolidated and cross-linked polymeric material, thereby forming a medical implant containing an antioxidant-doped cross-linked polymeric material. Medical implants containing cross-linked polymeric materials that are obtainable by the above methods also are provided.

Yet in another aspect, the invention provides methods of making a non-permanent medical device containing cross-linked polymeric material comprising: a) doping a manufactured medical device containing consolidated polymeric material with an antioxidant by diffusion, thereby forming an antioxidant-doped polymeric material; and b) annealing the antioxidant-doped polymeric material in liquid or gaseous environment and under various temperature and pressure conditions, for example, in boiling water under atmospheric pressure; c) irradiating the medical device with ionizing radiation, thereby forming a cross-linked polymeric material.

In another aspect, the invention provides non-oxidizing cross-linked polymeric materials with detectable residual free radicals.

In another aspect, the invention provides non-oxidizing cross-linked medical implants, including permanent and non-permanent medical devices, with detectable residual free radicals.

In another aspect, the invention provides non-oxidizing cross-linked medical implants, including permanent and non-permanent medical devices, with detectable residual free radicals and with a gradient of antioxidant.

In another aspect, the invention provides methods of making a medical implant comprising: a) providing a polymeric material; b) consolidating the polymeric material; c) machining the consolidated polymeric material, thereby forming a medical implant; d) irradiating the medical implant with ionizing radiation, thereby forming a cross-linked medical implant; e) doping the medical implant with an antioxidant by diffusion, thereby forming an antioxidant-doped cross-linked medical implant; and f) annealing the antioxidant-doped cross-linked medical implant in liquid or gaseous environment and under various temperature and pressure conditions, for example, in boiling water under atmospheric pressure.

Yet in another aspect, the invention provides methods of making a medical implant comprising: a) providing a consolidated polymeric material; b) machining the consolidated polymeric material, thereby forming a medical implant; c) irradiating the medical implant with ionizing radiation, thereby forming an antioxidant-doped cross-linked medical implant; d) doping the medical implant with an antioxidant by diffusion, thereby forming an antioxidant-doped cross-linked medical implant; and e) annealing the antioxidant-doped cross-linked medical implant in liquid or gaseous environment and under various temperature and pressure conditions, for example, in boiling water under atmospheric pressure.

In another aspect, the invention provides methods of making a medical implant comprising: a) providing a polymeric material; b) consolidating the polymeric material; c) machining the consolidated polymeric material, thereby forming a medical implant; d) doping the medical implant with an antioxidant by diffusion, thereby forming an antioxidant-doped medical implant; e) annealing the antioxidant-doped medical implant in liquid or gaseous environment and under various temperature and pressure conditions, for example, in boiling water under atmospheric pressure; and f) irradiating the medical implant with ionizing radiation, thereby forming an antioxidant-doped cross-linked medical implant.

Yet in another aspect, the invention provides methods of making a medical implant comprising: a) providing a consolidated polymeric material; b) machining the consolidated polymeric material, thereby forming a medical implant; c) doping the medical implant with an antioxidant by diffusion, thereby forming an antioxidant-doped medical implant; d) annealing the antioxidant-doped medical implant in liquid or gaseous environment and under various temperature and pressure conditions, for example, in boiling water under atmospheric pressure; and e) irradiating the medical implant with ionizing radiation, thereby forming an antioxidant-doped cross-linked medical implant.

In another aspect, the invention provides methods of making a medical implant comprising: a) providing a polymeric material; b) consolidating the polymeric material; c) irradiating the polymeric material with ionizing radiation, thereby forming a cross-linked polymeric material; d) doping the polymeric material with an antioxidant by diffusion, thereby forming an antioxidant-doped cross-linked polymeric material; e) annealing the antioxidant-doped cross-linked polymeric material in liquid or gaseous environment and under various temperature and pressure conditions, for example, in boiling water under atmospheric pressure; and f) machining the polymeric material, thereby forming an antioxidant-doped cross-linked medical implant.

Yet in another aspect, the invention provides methods of making a medical implant comprising: a) providing a consolidated polymeric material; b) irradiating the polymeric material with ionizing radiation, thereby forming a cross-linked polymeric material; c) doping the polymeric material with an antioxidant by diffusion, thereby forming an antioxidant-doped cross-linked polymeric material; d) annealing the antioxidant-doped cross-linked polymeric material in liquid or gaseous environment and under various temperature and pressure conditions, for example, in boiling water under atmospheric pressure; and e) machining the polymeric material, thereby forming an antioxidant-doped cross-linked medical implant.

Another aspect of the invention provides methods of making a medical implant comprising: a) providing a polymeric material; b) compression molding the polymeric material, thereby forming a medical implant; c) doping the medical implant containing an interface or an interlocked hybrid material with an antioxidant by diffusion, thereby forming an antioxidant-doped medical implant; d) annealing the antioxidant-doped medical implant in liquid or gaseous environment and under various temperature and pressure conditions, for example, in boiling water under atmospheric pressure; e)

packaging the medical implant; and f) irradiating the packaged medical implant by ionizing radiation, thereby forming an antioxidant-doped cross-linked and sterile medical implant. In another aspect, the polymeric material is compression molded to another piece or a medical implant, thereby form an interface or an interlocked hybrid material.

Another aspect of the invention provides methods of making a medical implant comprising: a) providing a compression molded polymeric material forming a medical implant; b) doping the medical implant containing an interface or an interlocked hybrid material with an antioxidant by diffusion, thereby forming an antioxidant-doped medical implant; c) annealing the antioxidant-doped medical implant in liquid or gaseous environment and under various temperature and pressure conditions, for example, in boiling water under atmospheric pressure; d) packaging the medical implant; and e) irradiating the packaged medical implant by ionizing radiation, thereby forming an antioxidant-doped cross-linked and sterile medical implant. In another aspect, the polymeric material is compression molded to another piece or a medical implant, thereby form an interface or an interlocked hybrid material.

Medical implants containing cross-linked polymeric materials that are obtainable by the all of the above methods also are provided.

Another aspect of the invention provides methods to increase the uniformity of an antioxidant in a doped polymeric material by annealing the doped polymeric material below the melting point of the doped polymeric material, for example, annealing in a liquid or a gaseous environment and under various temperature and pressure conditions, for example, in boiling water under atmospheric pressure or under pressure in order to anneal at a temperature above 100° C. and below the melting point of the polymeric material. In another aspect, doping or annealing of polymeric materials prior to machining can be carried out at a temperature above the melting point of the polymeric material, for example, at 150° C., 160° C., 170° C., 180° C., or higher.

Another aspect of the invention provides methods to increase the uniformity of an antioxidant in a doped polymeric material by annealing the doped polymeric material above the melting point of the doped polymeric material.

According to another aspect of the invention, the annealing of antioxidant-doped-polymeric material, -cross-linked polymeric material, or -medical implants, as described above, also can be carried out in a fluid, for example, water or mineral oil, under pressure at a temperature below or above 100° C. and below the melting point of the polymeric material.

According to another aspect of the invention, the doping of medical implant or polymeric material or cross-linked polymeric material with an antioxidant, as described herein, can be carried out in an antioxidant-emulsion, antioxidant-solution such as antioxidant-NaCl solution, or -mixture.

According to another aspect of the invention, the annealing of antioxidant-doped-polymeric material, -cross-linked polymeric material, or -medical implants, as described above, also can be carried out in antioxidant-emulsion, antioxidant-solution such as antioxidant-NaCl solution, or -mixture, under atmospheric pressure or under pressure at a temperature below or above 100° C. and below the melting point of the polymeric material and for a time period between about 1 minute and about 30 days. In another aspect, annealing of antioxidant-doped-polymeric materials or antioxidant-doped-cross-linked polymeric materials prior to machining can be carried out at a temperature above the melting point of the polymeric material, for example, at 150° C., 160° C., 170° C., 180° C., or higher.

BRIEF DESCRIPTION OF THE DRAWINGS

FIG. 6A shows vitamin E profiles obtained in vitamin E doped cubes that were machined from a 100 kGy irradiated UHMWPE (solid marks) and the vitamin E profiles of the doped cubes after annealing in boiling water (hollow marks).

FIG. 7A depicts vitamin E profiles obtained from the 24 hour doped cubes.

DETAILED DESCRIPTION OF THE INVENTION

Figure 1:
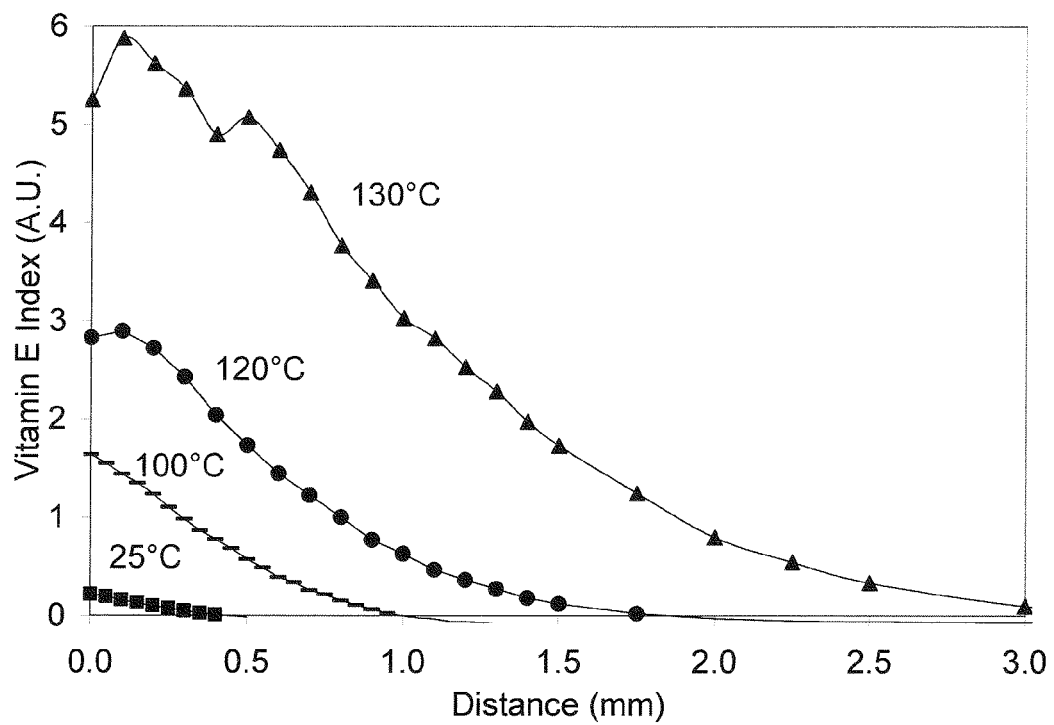
FIG. 1 shows penetration depth of vitamin E diffusion into UHMWPE at room temperature, 100° C., 120° C. and 130° C.

The present invention provides methods of making oxidation resistant medical implants that comprise medical devices, including permanent and non-permanent devices, and packaging that comprises polymeric material, such as polyethylene. The invention pertains to methods of doping consolidated polyethylene, such as UHMWPE, with antioxidants, before, during, or after crosslinking the consolidated polyethylene, and subsequent annealing in a liquid or a gaseous environment under various temperature and pressure conditions.

In one aspect of the invention, the doping of consolidated polyethylene can be carried out by diffusion of an antioxidant, for example, α-tocopherol, such as vitamin E. According to one aspect of the invention, the diffusion of the antioxidant is accelerated by increasing the temperature and/or pressure.

In another aspect, antioxidant doped consolidated polyethylene is subsequently annealed in a liquid or a gaseous environment and under various temperature and pressure conditions.

According to another aspect of the invention, an antioxidant is delivered in various forms, including in a pure form, for example, as pure vitamin E, or dissolved in a solvent.

According to another aspect of the invention, diffusion rate of an antioxidant into the polyethylene is increased by increasing the concentration of the antioxidant solution, for example, a vitamin E solution.

In accordance with another aspect of the invention, diffusion rate of an antioxidant into the polyethylene is increased by swelling the consolidated polyethylene in a supercritical fluid, for example, in a supercritical $CO_2$, i.e., the temperature being above the supercritical temperature, which is 31.3° C., and the pressure being above the supercritical pressure, which is 73.8 bar.

In general, for example, in case of vitamin E, as the antioxidant, mixing the resin powder, flakes, particles, or a mixture thereof, with vitamin E and consolidation thereafter result in changes in color of polymeric material to yellow. According to the instant invention, doping subsequent to consolidation avoids the exposure of vitamin E to high temperatures and pressures of consolidation and prevents the discoloration of the polymeric material. The invention also decreases the thermal effects on the antioxidant. The thermal effects can reduce the effectiveness of the antioxidant in protecting the polymeric material against oxidation.

Doping in the consolidated state also allows one to achieve a gradient of antioxidant in consolidated polymeric material. One can dope a certain thickness surface layer where the oxidation of the polymeric material in a medical device is of concern in terms of wear. This can be achieved by simply dipping or soaking finished devices, for example, a finished medical implant, for example, in pure vitamin E or in a solution of vitamin E or an emulsion of vitamin E at a given temperature and for a given amount of time.

Doping after crosslinking can result in an elevated antioxidant concentration near the surface and can increase the oxidative stability of the surface and near surface polyethylene in case of the diffusion of the antioxidant out of polyethylene. Generally, the antioxidant (for example, vitamin E) diffuses out of the polyethylene either during shelf storage and/or during in vivo use, which results in a surface region depleted from the antioxidant, and therefore the surface becomes less oxidation resistant. If polyethylene powder is blended with antioxidant before consolidation, the amount of the antioxidant can be increased to prevent surface depletion. However, higher concentrations of antioxidant in the blend would decrease the level of crosslink density and thus increase wear rates. According to the invention, the surface concentration of the antioxidant can be tailored to be higher than the bulk. Therefore, even with diffusion of the antioxidant out of the polyethylene, there will be no substantial depletion of the antioxidant and oxidation resistance will be maintained.

The emulsion of vitamin E can be a mixture of water and vitamin E and/or di-methyl sulfoxide (DMSO) and vitamin-E, mineral oil, or any other hydrophilic fluid and vitamin E. The emulsion can be maintained by stirring. The doping in the emulsion can be carried out at any temperature for any amount of time, both can be varied to achieve a certain penetration level of vitamin E into the UHMWPE sample or implant. The concentration of vitamin E in the emulsion can vary between about 1% (by volume) and 99% (by volume). Preferably, 30% (by volume) vitamin E can be used. The emulsion also can be formed by adding vitamin E into a mixture of hydrophilic fluids, such as a mixture of water and/or DMSO. The emulsion also can be formed by adding a solution of vitamin E, such as vitamin E/ethanol mixture into a hydrophilic fluid or a mixture of hydrophilic fluid. The solution of vitamin E used also can be made by a mixture of solvents. The emulsion also can be prepared by heating the components of the emulsion separately and mixing the heated components together, for example, an emulsion can be prepared by heating water to about 100° C. and heating the vitamin E to about 100° C., and then by mixing the two heated materials together.

Figure 4:
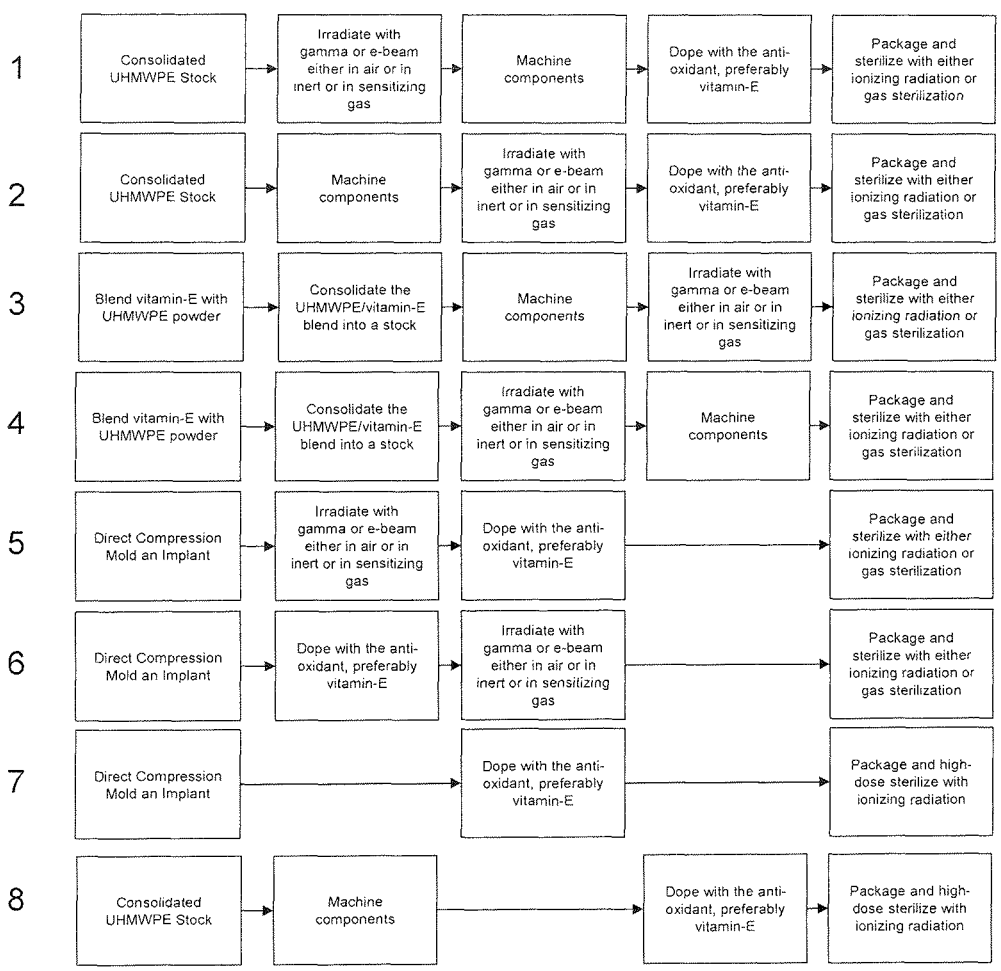
FIG. 4 schematically shows examples of sequences of processing UHMWPE and doping at various steps.
Figure 5:
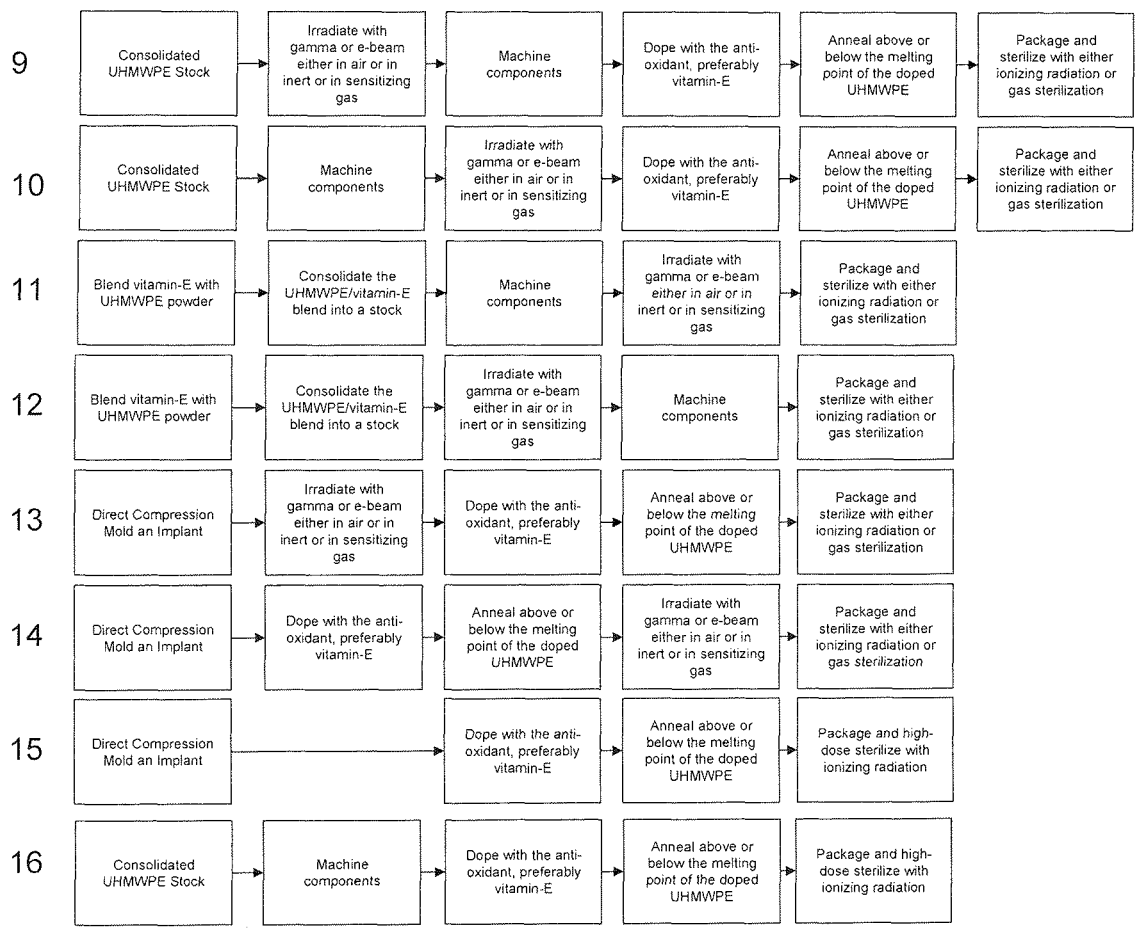
FIG. 5 schematically shows examples of sequences of processing UHMWPE and doping at various steps.

According to the methods described herein, an antioxidant, for example, vitamin E, can be doped into the polymeric material either before, during, or after irradiation (See for example, FIGS. 4 and 5).

It may be possible that the doped antioxidant can leach out of the polymeric material used in fabrication of medical implants or medical devices either during storage prior to use or during in vivo service. For a permanent medical device, the in vivo duration can be as long as the remaining life of the patient, which is the length of time between implantation of the device and the death of the patient, for example, 1-120 years, typically 5-30 years. If leaching out of the antioxidant is an issue, the irradiation of the medical implant or medical device or irradiation of any portion thereof can be carried out after doping the antioxidant. This can ensure crosslinking of the antioxidant to the host polymer through covalent bonds and thereby prevent loss of antioxidant from the medical implant or the device. Alternatively, the surface concentration of the antioxidant can be kept high enough that any leeching out of the antioxidant will not adversely affect oxidation resistance and/or other desired properties of the polyethylene imparted by the presence of the anti-oxidant. In one aspect of the invention, the implant can be doped a second time after the annealing step to increase the surface concentration level of the antioxidant.

According to another aspect of the invention, polymeric material, for example, resin powder, flakes, particles, or a mixture thereof, is mixed with an antioxidant and then the mixture is consolidated. The consolidated antioxidant doped polymeric material can be machined to use as a component in a medical implant or as a medical device.

According to another aspect of the invention, consolidated polymeric material, for example, consolidated resin powder, molded sheet, blown films, tubes, balloons, flakes, particles, or a mixture thereof, can be doped with an antioxidant, for example, vitamin E in the form of α-Tocopherol, by diffusion. Consolidated polymeric material, for example, consolidated UHMWPE can be soaked in 100% vitamin E or in a solution of α-Tocopherol in an alcohol, for example, ethanol or isopropanol or in an emulsion or mixture of vitamin E and water and/or di-methyl sulfoxide (DMSO). A solution of α-Tocopherol, about 50% by weight in ethanol can be used to diffuse in to UHMWPE in contact with a supercritical fluid, such as $CO_2$. The balloons, for example, PeBAX®, Nylon, and PET balloons can be doped with vitamin E and irradiated before, during, or after doping.

In another aspect, antioxidant doped consolidated polymeric material is subsequently annealed in a liquid or a gaseous environment and under various temperature and pressure conditions, for example, in boiling water under atmospheric pressure or under pressure in order to anneal at a temperature above 100° C. and below the melting point of the polymeric material. In another aspect, annealing of antioxidant-doped-consolidated polymeric materials or antioxidant-doped-consolidated cross-linked polymeric materials prior to machining can be carried out at a temperature above the melting point of the polymeric material, for example, at 150° C., 160° C., 170° C., 180° C., or higher.

The invention also relates to the following processing steps to fabricate medical devices made out of highly cross-linked polyethylene and containing metallic pieces such as bipolar hip replacements, tibial knee inserts with reinforcing metallic and polyethylene posts, intervertebral disc systems, and for any implant that contains a surface that cannot be readily sterilized by a gas sterilization method.

According to one aspect of the invention, the polyethylene component of a medical implant is in close contact with another material, such as a metallic mesh or back, a non-metallic mesh or back, a tibial tray, a patella tray, or an acetabular shell, wherein the polyethylene, such as resin powder, flakes and particles are directly compression molded to these counter faces. For example, a polyethylene tibial insert is manufactured by compression molding of polyethylene resin powder to a tibial tray, to a metallic mesh or back or to a non-metallic mesh or back. In the latter case, the mesh is shaped to serve as a fixation interface with the bone, through either bony in-growth or the use of an adhesive, such as polymethylmethacrylate (PMMA) bone cement. These shapes are of various forms including, acetabular liner, tibial tray for total or unicompartmental knee implants, patella tray, and glenoid component, ankle, elbow or finger component. Another aspect of the invention relates to mechanical interlocking of the molded polyethylene with the other piece(s), for example, a metallic or a non-metallic piece, that makes up part of the implant.

The interface geometry is crucial in that polyethylene assumes the geometry as its consolidated shape. Polyethylene has a remarkable property of 'shape memory' due to its very high molecular weight that results in a high density of physical entanglements. Following consolidation, plastic deformation introduces a permanent shape change, which attains a preferred high entropy shape when melted. This recovery of the original consolidated shape is due to the 'shape memory', which is achieved when the polyethylene is consolidated.

The recovery of polymeric material when subjected to annealing in an effort to quench residual free radicals is also problematic in medical devices that have a high degree of orientation. Balloon catheters often can have intended axial and radial alignment of the polymeric chains. Balloon catheters made from polyethylene benefit from the improved wear resistance generated from crosslinking when used with stents. Additionally, the use of catheters and stents coated with drugs precludes the use of ethylene oxide sterilization in some cases; thus ionizing radiation must be used, and the balloon catheter has to be protected from the deleterious effects of free-radical induced oxidation. Annealing of these materials close to the melt transition temperature would result in bulk chain motion and subsequent loss of dimensional tolerances of the part. By diffusing 100% vitamin E or in a solution of α-Tocopherol in an alcohol, for example, ethanol or isopropanol, into the medical device, such as a balloon catheter, either before, during, or after exposure to ionizing radiation for either crosslinking or sterilization, the problems associated with post-irradiation oxidation can be avoided without the need for thermal treatment. As described herein, the balloons, for example, PeBAX®, Nylon, and PET balloons can be doped with vitamin E and irradiated before, during, or after doping.

Another aspect of the invention provides that following the compression moldings of the polyethylene to the counterface with the mechanical interlock, the hybrid component is irradiated using ionizing radiation to a desired dose level, for example, about 25 kGy to about 1000 kGy, preferably between about 30 kGy and about 150 kGy, more preferably between about 50 kGy and about 100 kGy. Another aspect of the invention discloses that the irradiation step generates residual free radicals and therefore, a melting step is introduced thereafter to quench the residual free radicals. Since the polyethylene is consolidated into the shape of the interface, thereby setting a 'shape memory' of the polymer, the polyethylene does not separate from the counterface.

In another aspect of the invention, there are provided methods of crosslinking polyethylene, to create a polyethylene-based medical device, wherein the device is immersed in a non-oxidizing medium such as inert gas or inert fluid, wherein the medium is heated to above the melting point of the irradiated polyethylene, for example, UHMWPE (above about 137° C.) to eliminate the crystalline matter and to allow the recombination/elimination of the residual free radicals. Because the shape memory of the compression molded polymer is set at the mechanically interlocked interface and that memory is strengthened by the crosslinking step, there is no significant separation at the interface between the polyethylene and the counterface.

Another aspect of the invention provides that following the above steps of free radical elimination, the interface between the metal and the polymer become sterile due to the high irradiation dose level used during irradiation. When there is substantial oxidation on the outside surface of the polyethylene induced during the free radical elimination step or irradiation step, the device surface can be further machined to remove the oxidized surface layer. In another aspect, the invention provides that in the case of a post-melting machining of an implant, the melting step can be carried out in the presence of an inert gas.

Another aspect of the invention includes methods of sterilization of the fabricated device, wherein the device is further sterilized with ethylene oxide, gas plasma, or the other gases, when the interface is sterile but the rest of the component is not.

In another aspect, the invention discloses packaging of irradiated and antioxidant-doped medical implants or medical devices including compression molded implants or devices, wherein the implants or the devices can be sterilized by ionizing radiation or gas sterilization to obtain sterile and cross-linked medical implants or medical devices.

Doping Conditions:

In one aspect of the invention, the vitamin E doping step can be carried out by soaking the UHMWPE article, implant, stock material (irradiated or unirradiated) in vitamin E or a solution of vitamin E or an emulsion of vitamin E. The vitamin E can be cycled through different temperatures during the doping. For example, the vitamin E can be first heated to a peak temperature, then cooled down to a valley temperature and then heated again. Peak temperature can be between about 50° C. and about 300° C., or between about 70° C. and about 150° C., or about 110° C., or about 105° C., or about 100° C. Valley temperature is always lower than the peak temperature. Valley temperature can be between about 0° C. and about 300° C., or between about 20° C. and about 90° C., or about 80° C., or about 70° C., or about 50° C., or about 25° C. The UHMWPE can be held at each peak or valley temperatures for different time periods. Each peak temperature cycle can be held for a time period between about 1 minute and about 30 days, preferably between about 1 hour and about 3 days, more preferably between about 2 hours and about 24 hours, and even more preferably for about 12 hours. Each valley temperature can be held for a time period between about 1 minute and about 30 days, preferably between about 1 hour and about 3 days, more preferably between 2 hours and 24 hours, and even more preferably for about 2 hours. The cooling and heating rates between cycles can be between about 1° C./min and about 100° C./min, preferably about 10° C./min. The heat-cool cycles can follow a step function or a sinusoidal function or any other function. The doping cycle can be of at least one step of heating to peak temperature, one step of holding at peak temperature, one step of cooling to valley temperature, or one step of holding at valley temperature. Alternatively, the number of steps can be increased to achieve a desired level of vitamin E penetration into the UHMWPE. The steps can be sequenced to cycle between a valley and a peak temperature. For example, soaking at 30° C. for 1 hour, heating to 105° C. or 110° C. at 10° C./min and soaking at 105° C. or 110° C. for 1 hour, cooling to 30° C. at 10° C./min, and repeating the same soak-heat-soak-cool cycle for 24 times. Alternatively, the cycling can be sequenced to consecutively hold at different temperatures for different time periods. For example, soaking at 30° C. for 1 hour, heating to 90° C. at 10° C./min and soaking at 90° C. for 1 hour, cooling to 30° C. at 10° C./min, and repeating the same soak-heat-soak-cool cycle for 24 times but varying the peak temperature between 90° C. and 110° C. at every other cycle.

The above described cycling the temperature also can be used in the water, air or other media annealing step of doped UHMWPE samples or implants.

The above described cycling the temperature also can be used in an antioxidant/hydrophilic solvent solution or emulsion media annealing step of doped UHMWPE samples or implants. For example, a mixture of about 30% vitamin E in about 70% water or about 70% di-methyl sulfoxide (DMSO) or about 70% vitamin E in about 30% water or 30% DMSO can be used. The water in the mixture also can contain NaCl.

Doping also can be completed in one step of soaking in a vitamin E solution or a vitamin E-emulsion, for example, the soaking can be carried out at room temperature or at an elevated temperature, for example, at about 100° C.

The vitamin E emulsion can be a mixture of vitamin E with a hydrophilic solvent such as water and/or dimethyl sulfoxide and/or NaCl or the like. The vitamin E emulsion can have a vitamin E concentration ranging from about 1% to about 99%. The vitamin E emulsion also can be prepared by mixing the vitamin E in mixture of hydrophilic fluids, such as a mixture of water and/or DMSO. The vitamin E emulsion also can be prepared by adding a solution of vitamin E into a hydrophilic fluid or a mixture of hydrophilic fluids or a mixture of a hydrophilic fluid with NaCl.

Doping of the polymer can be carried out in a vitamin E emulsion either at room temperature or at a temperature between room temperature and the boiling point of the hydrophilic fluid.

The vitamin E emulsion can be salinated by adding sodium chloride (NaCl) to the hydrophilic fluid and doping can be carried out in the salinated emulsion. Because the salination can elevate the boiling point of the hydrophilic fluid, the doping also can be carried out at a temperature higher than the boiling point of the non-salinated hydrophilic fluid.

The vitamin E emulsion can be doped at an elevated pressure to increase the boiling point of the hydrophilic fluid component of the emulsion.

The vitamin E emulsion can also be mixed with sodium hydroxide (NaOH) and doping can be carried out in an alkaline emulsion. Because the addition of NaOH can elevate the boiling point of the hydrophilic fluid, the doping also can be carried out at a temperature higher than the boiling point of the hydrophilic fluid. Since, the boiling point of a hydrophilic component of vitamin E emulsions or mixtures can be elevated, doping can be carried out at a temperature higher than the boiling point of the hydrophilic component, for example, doping temperature of a boiling vitamin E-water emulsion can be higher than 100° C., for example, about 105° C. or about 110° C.

Doping also can be carried out at an elevated pressure by soaking the polymer in vitamin E, vitamin E solution, or vitamin E emulsion, or a mixture thereof.

Figure 6A:
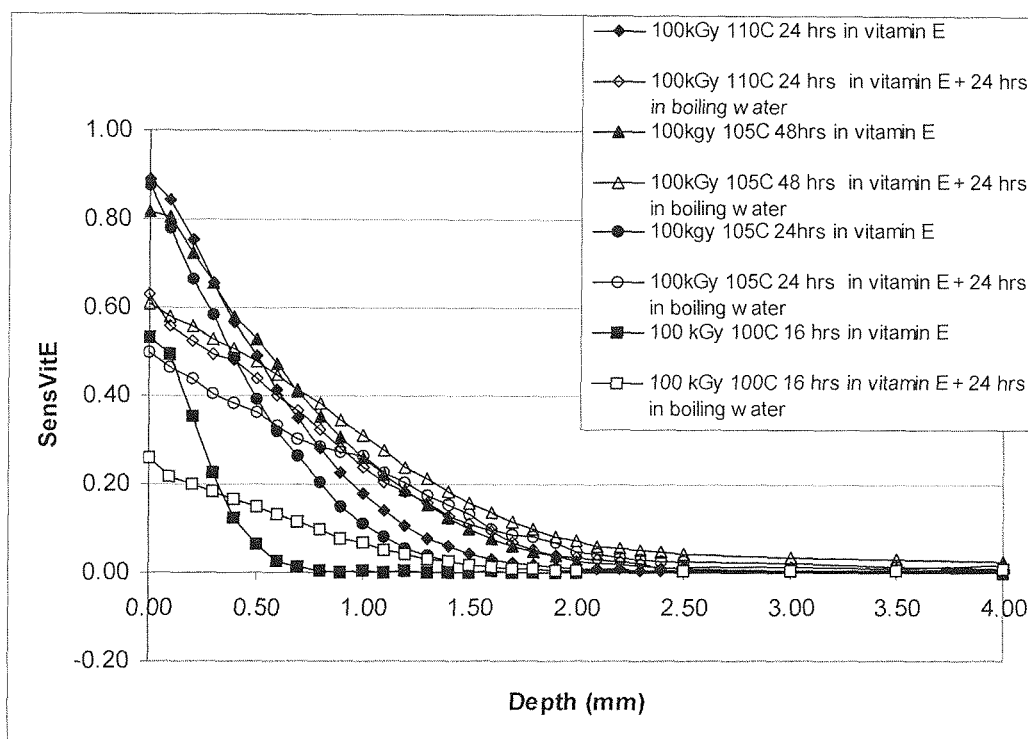
FIGS. 6A and B show depth-profiles of sensitive vitamin E index (sensVitE) for vitamin E doped UHMWPE cubes.
Figure 6B:
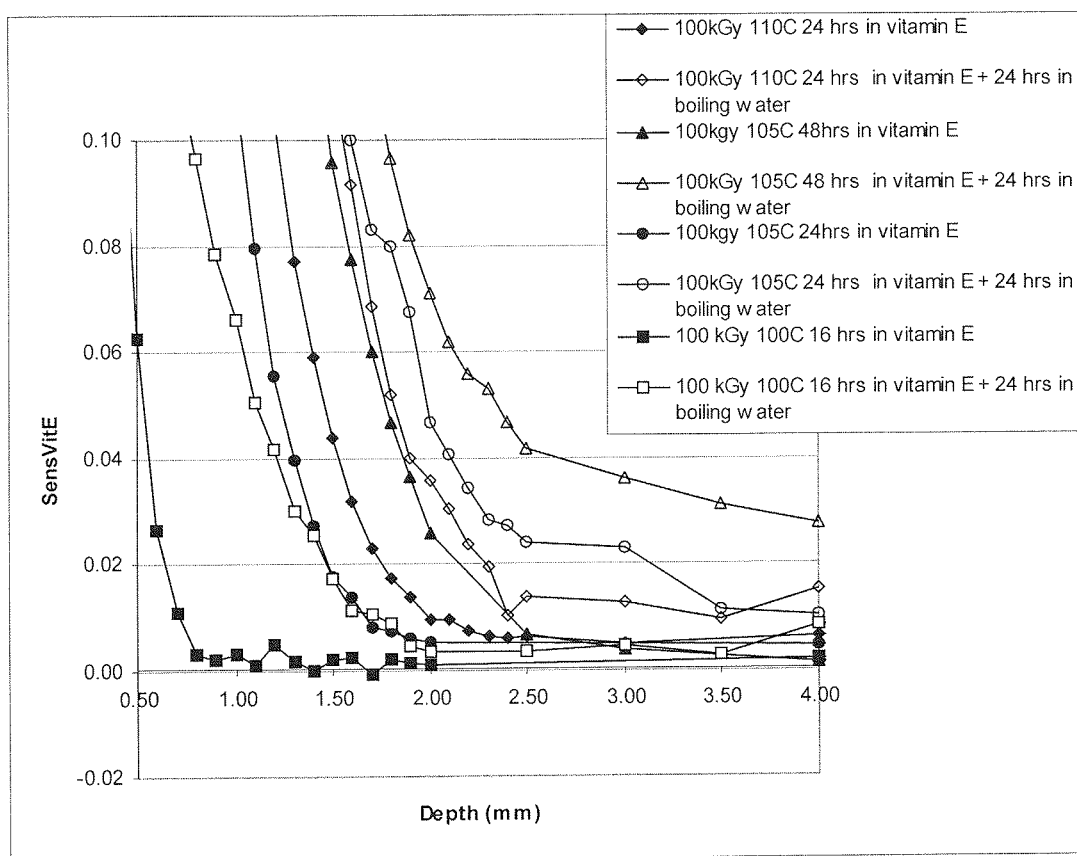
FIG. 6B shows the vitamin E penetration profiles at a higher resolution.

Doping and Post-Doping Annealing:

Referring to FIGS. 6A and 6B, the penetration depth of vitamin E into UHMWPE increased with increasing temperature of doping. Annealing in boiling water subsequent to doping increased the penetration depth of the vitamin E into UHMWPE. It also reduced the surface concentration of vitamin E. This method of annealing in boiling water can be used to increase the uniformity of the vitamin E distribution in UHMWPE. If desired, the decrease in the near surface concentration of vitamin E can be increased with subsequent additional doping cycles of vitamin E. If desired, the additional doping cycles also can be followed by annealing cycles, for example, in boiling water.

The annealing of antioxidant-doped UHMWPE also can be carried out in water at other temperatures, such as between room temperature and boiling point of water. Alternatively, the water also can be at a higher temperature, either in the form of steam or liquid. The liquid form of water at temperatures above the normal boiling point can be achieved by increasing the pressure. Irradiated and antioxidant-doped UHMWPE can be annealed in a pressure chamber in water at elevated temperatures and pressures to maintain the liquid or steam/gaseous state of water.

Figure 7A:
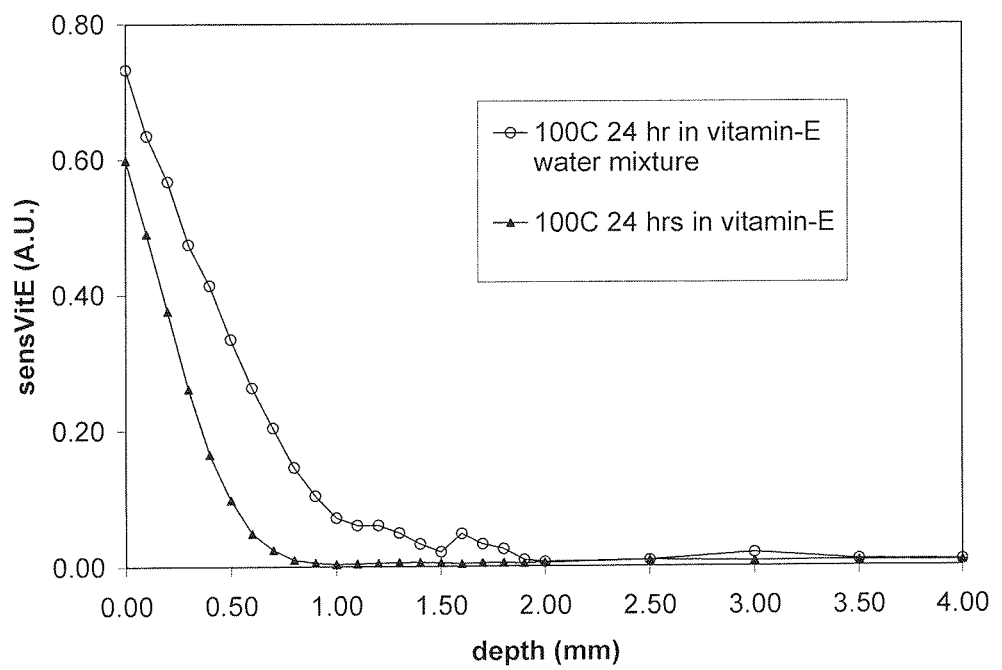
FIGS. 7A and B show depth-profiles of sensitive vitamin E index (sensVitE) for vitamin E doped and vitamin E-water mixture doped UHMWPE cubes.
Figure 7B:
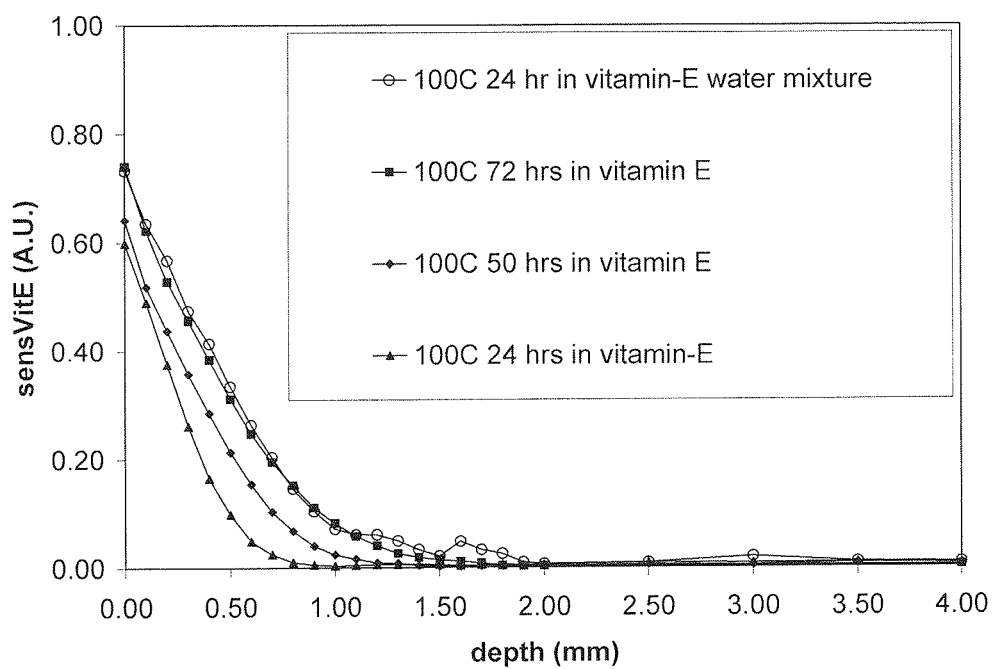
FIG. 7B shows the sensVitE profiles of cubes doped for various time period at 100° C.

Referring to FIGS. 7A and 7B, the depth-profiles of sensitive vitamin E index (sensVitE) indicate doping at 100° C. in vitamin E emulsion resulted in a higher vitamin E surface concentration and a deeper vitamin E penetration than the UHMWPE cubes that were doped in vitamin E alone. Doping for 24 hours at 100° C. in the vitamin E emulsion resulted in a diffusion profile equivalent to a 72 hours of doping in vitamin E alone (see FIG. 7B).

Annealing of vitamin E emulsion-doped UHMWPE in boiling water subsequent to doping can increase the penetration depth of the vitamin E into UHMWPE. It also can reduce the surface concentration of vitamin E. This method of annealing vitamin E emulsion-doped UHMWPE in boiling water can be used to increase the uniformity of the vitamin E distribution in UHMWPE. If desired, the decrease in the near surface concentration of vitamin E can be increased with subsequent additional doping cycles of vitamin E or vitamin E emulsion. If desired, the additional doping cycles also can be followed by annealing cycles, for example, in boiling water or in boiling vitamin E emulsion.

The annealing of antioxidant-emulsion-doped UHMWPE also can be carried out in antioxidant-emulsion at other temperatures, such as between room temperature and boiling point of the hydrophilic component of the emulsion. Alternatively, the antioxidant-emulsion also can be at a higher temperature, either in the form of steam or liquid. For example, the liquid form of the hydrophilic component of the emulsion can be at a temperature above its normal boiling point, which can be achieved by increasing the pressure. Irradiated and antioxidant-emulsion-doped UHMWPE can be annealed in a pressure chamber containing the emulsion at elevated temperatures and pressures.

The above annealing methods also can be applied to a finished article, such as a medical implant. The implant can be machined from an irradiated UHMWPE. Alternatively, the implant can be direct compression molded from UHMWPE powder and subsequently irradiated. The implant can be doped with vitamin E or vitamin E emulsion and subsequently annealed. In another aspect, the doping can be carried out by soaking the implant in vitamin E, vitamin E emulsion, or vitamin E solution, heated to a temperature between room temperature and about 145° C., preferably between about 50° C. and about 140° C., more preferably between about 90° C. and about 120° C., and even more preferably at about 105° C. or about 110° C. The doping can be carried out for a time period between about 1 minute and about 30 days, preferably between about 1 hour and about 3 days, more preferably between about 10 hours and about 3 days, and even more preferably for about 24 hours. Subsequent to doping, the annealing can be carried out in a liquid medium, such as water, mineral oil, vitamin E emulsion, vitamin E solution, etc. The annealing can be carried out by soaking the implant in the liquid medium, for example, in water or in vitamin E emulsion, or in vitamin E solution, at an elevated temperature of between about room temperature and about 100° C., more preferably between about 50° C. and about 100° C., and even more preferably at about 100° C. The annealing in the liquid medium, for example, in water or in vitamin E emulsion, also can be carried out in steam at different temperatures. The annealing can be carried out for a time period between about 1 minute and about 30 days, preferably between about 1 hour and about 3 days, more preferably between about 10 hours and about 3 days, and even more preferably for about 24 hours.

The post-doping annealing, for example, in boiling water, results in deeper antioxidant (for example, α-tocopherol, such as vitamin E) penetration into the irradiated UHMWPE. The deeper penetration of antioxidant is advantageous in many ways. Deeper penetration of the antioxidant protects a thicker surface layer of the polyethylene against oxidation. In some cases, if the penetration is deep enough, a minimum concentration of antioxidant is achieved throughout the irradiated UHMWPE and also provide oxidation resistance throughout the irradiated UHMWPE.

Following annealing, the implant can be further doped with vitamin E or vitamin E emulsion to increase the surface concentration of vitamin E that may have decreased during the annealing cycle.

The annealing cycle can be followed by an industrial washing cycle, for example, a dishwasher cycle. The washing cycle also can be considered as the annealing cycle.

The annealing of doped polymeric material can be conducted under any suitable liquid or gaseous environment, under various temperature and pressure conditions, for example, in boiling water under atmospheric pressure or under pressure in order to anneal at a temperature above 100° C. and below the melting point of UHMWPE. In another aspect, annealing of antioxidant-doped-polymeric materials or antioxidant-doped-cross-linked polymeric materials prior to machining can be carried out at a temperature above the melting point of the polymeric material, for example, at 150° C., 160° C., 170° C., 180° C., or higher.

The annealing of doped polymeric material also can be carried out in a fluid, for example, water, vitamin E emulsion, vitamin E solution, or mineral oil, under pressure at a temperature above 100° C. and below the melting point of the polymeric material or above the melting point of the polymeric materials prior to machining, for example, at 150° C., 160° C., 170° C., 180° C., or higher.

The above doping and post-doping annealing steps can also be used with an annealing step, as described above, before prior to doping; for example, the polymeric material or the medical implant can be boiled in water and then doped, or boiled in water and then doped, and annealed.

The above doping and post-doping annealing techniques also can be used with any anti-oxidant or any other additive.

Methods of doping, post-doping annealing, and making oxidation resistant polymeric material are also disclosed in U.S. application Ser. No. 10/757,551, filed Jan. 15, 2004, the entirety of which is incorporated herewith by reference.

DEFINITIONS

Definitions of various terms used in this application are provided herewith in order to illustrate certain aspects of the invention.

"Antioxidant" refers to what is known in the art as (see, for example, WO 01/80778, U.S. Pat. No. 6,448,315). Alpha- and delta-tocopherol; propyl, octyl, or dedocyl gallates; lactic, citric, and tartaric acids and their salts; orthophosphates, tocopherol acetate. Preferably vitamin E.

The term "antioxidant-emulsion" or "antioxidant-solution" for example, "vitamin E emulsion" or "vitamin E solution" refers to a mixture or solution of vitamin E (α-Tocopherol) and water, mineral oil, or any other hydrophilic fluid and/or di-methyl sulfoxide (DMSO) and/or NaCl and/or NaOH or a mixture thereof. The mixture can be a mixture of the antioxidant, for example, vitamin E, in an alcohol, for example, ethanol or isopropanol in a hydrophilic fluid or a mixture of the hydrophilic fluids. The concentration of an antioxidant, for example, vitamin E, in an emulsion can vary between about 1% (by volume) and 99% (by volume).

"Supercritical fluid" refers to what is known in the art, for example, supercritical propane, acetylene, carbon dioxide ($CO_2$). In this connection the critical temperature is that temperature above which a gas cannot be liquefied by pressure alone. The pressure under which a substance may exist as a gas in equilibrium with the liquid at the critical temperature is the critical pressure. Supercritical fluid condition generally means that the fluid is subjected to such a temperature and such a pressure that a supercritical fluid and thereby a supercritical fluid mixture is obtained, the temperature being above the supercritical temperature, which for $CO_2$ is 31.3° C., and the pressure being above the supercritical pressure, which for $CO_2$ is 73.8 bar. More specifically, supercritical condition refers to a condition of a mixture, for example, UHMWPE with an antioxidant, at an elevated temperature and pressure, when a supercritical fluid mixture is formed and then evaporate $CO_2$ from the mixture, UHMWPE doped with an antioxidant is obtained (see, for example, U.S. Pat. No. 6,448,315 and WO 02/26464)

The term "compression molding" as referred herein related generally to what is known in the art and specifically relates to high temperature molding polymeric material wherein polymeric material is in any physical state, including powder form, is compressed into a slab form or mold of a medical implant, for example, a tibial insert, an acetabular liner, a glenoid liner, a patella, or an unicompartmental insert, can be machined.

The term "direct compression molding" as referred herein related generally to what is known in the art and specifically relates to molding applicable in polyethylene-based devices, for example, medical implants wherein polyethylene in any physical state, including powder form, is compressed to solid support, for example, a metallic back, metallic mesh, or metal surface containing grooves, undercuts, or cutouts. The compression molding also includes high temperature compression molding of polyethylene at various states, including resin powder, flakes and particles, to make a component of a medical implant, for example, a tibial insert, an acetabular liner, a glenoid liner, a patella, or an unicompartmental insert.

The term "mechanically interlocked" refers generally to interlocking of polyethylene and the counterface, that are produced by various methods, including compression molding, heat and irradiation, thereby forming an interlocking interface, resulting into a 'shape memory' of the interlocked polyethylene. Components of a device having such an interlocking interface can be referred to as a "hybrid material". Medical implants having such a hybrid material, contain a substantially sterile interface.

The term "substantially sterile" refers to a condition of an object, for example, an interface or a hybrid material or a medical implant containing interface(s), wherein the interface is sufficiently sterile to be medically acceptable, i.e., will not cause an infection or require revision surgery.

"Metallic mesh" refers to a porous metallic surface of various pore sizes, for example, 0.1-3 mm. The porous surface can be obtained through several different methods, for example, sintering of metallic powder with a binder that is subsequently removed to leave behind a porous surface; sintering of short metallic fibers of diameter 0.1-3 mm; or sintering of different size metallic meshes on top of each other to provide an open continuous pore structure.

"Bone cement" refers to what is known in the art as an adhesive used in bonding medical devices to bone. Typically, bone cement is made out of polymethylmethacrylate (PMMA).

"High temperature compression molding" refers to the compression molding of polyethylene in any form, for example, resin powder, flakes or particles, to impart new geometry under pressure and temperature. During the high temperature (above the melting point of polyethylene) compression molding, polyethylene is heated to above its melting point, pressurized into a mold of desired shape and allowed to cool down under pressure to maintain a desired shape.

"Shape memory" refers to what is known in the art as the property of polyethylene, for example, an UHMWPE, that attains a preferred high entropy shape when melted. The preferred high entropy shape is achieved when the resin powder is consolidated through compression molding.

The phrase "substantially no detectable residual free radicals" refers to a state of a polyethylene component, wherein enough free radicals are eliminated to avoid oxidative degradation, which can be evaluated by electron spin resonance (ESR). The phrase "detectable residual free radicals" refers to the lowest level of free radicals detectable by ESR or more. The lowest level of free radicals detectable with state-of-the-art instruments is about $10^{14}$ spins/gram and thus the term "detectable" refers to a detection limit of $10^{14}$ spins/gram by ESR.

The terms "about" or "approximately" in the context of numerical values and ranges refers to values or ranges that approximate or are close to the recited values or ranges such that the invention can perform as intended, such as having a desired degree of crosslinking and/or a desired lack of free radicals, as is apparent to the skilled person from the teachings contained herein. This is due, at least in part, to the varying properties of polymer compositions. Thus these terms encompass values beyond those resulting from systematic error.

Polymeric Material: Ultra-high molecular weight polyethylene (UHMWPE) refers to linear non-branched chains of ethylene having molecular weights in excess of about 500,000, preferably above about 1,000,000, and more preferably above about 2,000,000. Often the molecular weights can reach about 8,000,000 or more. By initial average molecular weight is meant the average molecular weight of the UHMWPE starting material, prior to any irradiation. See U.S. Pat. No. 5,879,400, PCT/US99/16070, filed on Jul. 16, 1999, and PCT/US97/02220, filed Feb. 11, 1997.

The products and processes of this invention also apply to various types of polymeric materials, for example, any polyolefin, including high-density-polyethylene, low-density-polyethylene, linear-low-density-polyethylene, ultra-high molecular weight polyethylene (UHMWPE), or mixtures thereof. Polymeric materials, as used herein, also applies to polyethylene of various forms, for example, resin powder, flakes, particles, powder, or a mixture thereof, or a consolidated form derived from any of the above.

Crosslinking Polymeric Material: Polymeric Materials, for example, UHMWPE can be cross-linked by a variety of approaches, including those employing cross-linking chemicals (such as peroxides and/or silane) and/or irradiation. Preferred approaches for cross-linking employ irradiation. Cross-linked UHMWPE also can be obtained according to the teachings of U.S. Pat. No. 5,879,400, U.S. Pat. No. 6,641,617, and PCT/US97/02220.

Consolidated Polymeric Material: "Consolidated polymeric material refers" to a solid, consolidated bar stock, solid material machined from stock, or semi-solid form of polymeric material derived from any forms as described herein, for example, resin powder, flakes, particles, or a mixture thereof, that can be consolidated. The consolidated polymeric material also can be in the form of a slab, block, solid bar stock, machined component, film, tube, balloon, pre-form, implant, or finished medical device.

The term "non-permanent device" refers to what is known in the art as a device that is intended for implantation in the body for a period of time shorter than several months. Some non-permanent devices could be in the body for a few seconds to several minutes, while other may be implanted for days, weeks, or up to several months. Non-permanent devices include catheters, tubing, intravenous tubing, and sutures, for example.

"Pharmaceutical compound", as described herein, refers to a drug in the form of a powder, suspension, emulsion, particle, film, cake, or molded form. The drug can be free-standing or incorporated as a component of a medical device.

The term "pressure chamber" refers to a vessel or a chamber in which the interior pressure can be raised to levels above atmospheric pressure.

The term "packaging" refers to the container or containers in which a medical device is packaged and/or shipped. Packaging can include several levels of materials, including bags, blister packs, heat-shrink packaging, boxes, ampoules, bottles, tubes, trays, or the like or a combination thereof. A single component may be shipped in several individual types of package, for example, the component can be placed in a bag, which in turn is placed in a tray, which in turn is placed in a box. The whole assembly can be sterilized and shipped. The packaging materials include, but not limited to, vegetable parchments, multi-layer polyethylene, Nylon 6, polyethylene terephthalate (PET), and polyvinyl chloride-vinyl acetate copolymer films, polypropylene, polystyrene, and ethylene-vinyl acetate (EVA) copolymers.

The term "sealing" refers to the process of isolating a chamber or a package from the outside atmosphere by closing an opening in the chamber or the package. Sealing can be accomplished by a variety of means, including application of heat (for example, thermally-sealing), use of adhesive, crimping, cold-molding, stapling, or application of pressure.

The term "blister packs" refers to a packaging comprised of a rigid plastic bowl with a lid or the like that is either peeled or punctured to remove the packaged contents. The lid is often made of aluminum, or a gas-permeable membrane such as a Tyvek. The blister packs are often blow-molded, a process where the plastic is heated above its deformation temperature, at which point pressurized gas forces the plastic into the required shape.

The term "heat-shrinkable packaging" refers to plastic films, bags, or tubes that have a high degree of orientation in them. Upon application of heat, the packaging shrinks down as the oriented chains retract, often wrapping tightly around the medical device.

The term "intervertebral disc system" refers to an artificial disc that separates the vertebrae in the spine. This system can either be composed of one type of material, or can be a composite structure, for example, cross-linked UHMWPE with metal edges.

The term "balloon catheters" refers to what is known in the art as a device used to expand the space inside blood vessels or similar. Balloon catheters are usually thin wall polymeric devices with an inflatable tip, and can expand blocked arteries, stents, or can be used to measure blood pressure. Commonly used polymeric balloons include, for example, polyether-block co-polyamide polymer (PeBAX®), Nylon, and polyethylene terephthalate (PET) balloons. Commonly used polymeric material used in the balloons and catheters include, for example, co-polymers of polyether and polyamide (for example, PeBAX®), Polyamides, Polyesters (for example, PET), and ethylene vinyl alcohol (EVA) used in catheter fabrication.

Medical device tubing: Materials used in medical device tubing, including an intravenous tubing include, polyvinyl chloride (PVC), polyurethane, polyolefins, and blends or alloys such as thermoplastic elastomers, polyamide/imide, polyester, polycarbonate, or various fluoropolymers.

The term "stent" refers to what is known in the art as a metallic or polymeric cage-like device that is used to hold bodily vessels, such as blood vessels, open. Stents are usually introduced into the body in a collapsed state, and are inflated at the desired location in the body with a balloon catheter, where they remain.

"Melt transition temperature" refers to the lowest temperature at which all the crystalline domains in a material disappear.

The term "interface" in this invention is defined as the niche in medical devices formed when an implant is in a configuration where a component is in contact with another piece (such as a metallic or a non-metallic component), which forms an interface between the polymer and the metal or another polymeric material. For example, interfaces of polymer-polymer or polymer-metal are in medical prosthesis, such as orthopedic joints and bone replacement parts, for example, hip, knee, elbow or ankle replacements.

Medical implants containing factory-assembled pieces that are in close contact with the polyethylene form interfaces. In most cases, the interfaces are not readily accessible to ethylene oxide gas or the gas plasma during a gas sterilization process.

Irradiation: In one aspect of the invention, the type of radiation, preferably ionizing, is used. According to another aspect of the invention, a dose of ionizing radiation ranging from about 25 kGy to about 1000 kGy is used. The radiation dose can be about 25 kGy, about 50 kGy, about 65 kGy, about 75 kGy, about 85 kGy, about 100 kGy, about 150, kGy, about 200 kGy, about 300 kGy, about 400 kGy, about 500 kGy, about 600 kGy, about 700 kGy, about 800 kGy, about 900 kGy, or about 1000 kGy, or above 1000 kGy, or any integer thereabout or therebetween. Preferably, the radiation dose can be between about 25 kGy and about 150 kGy or between about 50 kGy and about 100 kGy. These types of radiation, including gamma and/or electron beam, kills or inactivates bacteria, viruses, or other microbial agents potentially contaminating medical implants, including the interfaces, thereby achieving product sterility. The irradiation, which may be electron or gamma irradiation, in accordance with the present invention can be carried out in air atmosphere containing oxygen, wherein the oxygen concentration in the atmosphere is at least 1%, 2%, 4%, or up to about 22%, or any integer thereabout or therebetween. In another aspect, the irradiation can be carried out in an inert atmosphere, wherein the atmosphere contains gas selected from the group consisting of nitrogen, argon, helium, neon, or the like, or a combination thereof. The irradiation also can be carried out in a vacuum.

In accordance with a preferred feature of this invention, the irradiation may be carried out in a sensitizing atmosphere. This may comprise a gaseous substance which is of sufficiently small molecular size to diffuse into the polymer and which, on irradiation, acts as a polyfunctional grafting moiety. Examples include substituted or unsubstituted polyunsaturated hydrocarbons; for example, acetylenic hydrocarbons such as acetylene; conjugated or unconjugated olefinic hydrocarbons such as butadiene and (meth)acrylate monomers; sulfur monochloride, with chloro-tri-fluoroethylene (CTFE) or acetylene being particularly preferred. By "gaseous" is meant herein that the sensitizing atmosphere is in the gas phase, either above or below its critical temperature, at the irradiation temperature.

Metal Piece: In accordance with the invention, the piece forming an interface with polymeric material is, for example, a metal. The metal piece in functional relation with polyethylene, according to the present invention, can be made of a cobalt chrome alloy, stainless steel, titanium, titanium alloy or nickel cobalt alloy, for example.

Non-metallic Piece: In accordance with the invention, the piece forming an interface with polymeric material is, for example, a non-metal. The non-metal piece in functional relation with polyethylene, according to the present invention, can be made of ceramic material, for example.

The term "inert atmosphere" refers to an environment having no more than 1% oxygen and more preferably, an oxidant-free condition that allows free radicals in polymeric materials to form cross links without oxidation during a process of sterilization. An inert atmosphere is used to avoid $O_2$, which would otherwise oxidize the medical device comprising a polymeric material, such as UHMWPE. Inert atmospheric conditions such as nitrogen, argon, helium, or neon are used for sterilizing polymeric medical implants by ionizing radiation.

Inert atmospheric conditions such as nitrogen, argon, helium, neon, or vacuum are also used for sterilizing interfaces of polymeric-metallic and/or polymeric-polymeric in medical implants by ionizing radiation.

Inert atmospheric conditions also refers to an inert gas, inert fluid, or inert liquid medium, such as nitrogen gas or silicon oil.

Anoxic environment: "Anoxic environment" refers to an environment containing gas, such as nitrogen, with less than 21%-22% oxygen, preferably with less than 2% oxygen. The oxygen concentration in an anoxic environment also can be at least 1%, 2%, 4%, 6%, 8%, 10%, 12% 14%, 16%, 18%, 20%, or up to about 22%, or any integer thereabout or therebetween.

The term "vacuum" refers to an environment having no appreciable amount of gas, which otherwise would allow free radicals in polymeric materials to form cross links without oxidation during a process of sterilization. A vacuum is used to avoid $O_2$, which would otherwise oxidize the medical device comprising a polymeric material, such as UHMWPE. A vacuum condition can be used for sterilizing polymeric medical implants by ionizing radiation.

A vacuum condition can be created using a commercially available vacuum pump. A vacuum condition also can be used when sterilizing interfaces of polymeric-metallic and/or polymeric-polymeric in medical implants by ionizing radiation.

Residual Free Radicals: "Residual free radicals" refers to free radicals that are generated when a polymer is exposed to ionizing radiation such as gamma or e-beam irradiation. While some of the free radicals recombine with each other to from crosslinks, some become trapped in crystalline domains. The trapped free radicals are also known as residual free radicals.

According to one aspect of the invention, the levels of residual free radicals in the polymer generated during an ionizing radiation (such as gamma or electron beam) is preferably determined using electron spin resonance and treated appropriately to reduce the free radicals.

Sterilization: One aspect of the present invention discloses a process of sterilization of medical implants containing polymeric material, such as cross-linked UHMWPE. The process comprises sterilizing the medical implants by ionizing sterilization with gamma or electron beam radiation, for example, at a dose level ranging from 25-70 kGy, or by gas sterilization with ethylene oxide or gas plasma.

Another aspect of the present invention discloses a process of sterilization of medical implants containing polymeric material, such as cross-linked UHMWPE. The process comprises sterilizing the medical implants by ionizing sterilization with gamma or electron beam radiation, for example, at a dose level ranging from 25-200 kGy. The dose level of sterilization is higher than standard levels used in irradiation. This is to allow crosslinking or further crosslinking of the medical implants during sterilization.

In another aspect, the invention discloses a process of sterilizing medical implants containing polymeric material, such as cross-linked UHMWPE, that is in contact with another piece, including polymeric material consolidated by compression molding to another piece, thereby forming an interface and an interlocked hybrid material, comprising sterilizing an interface by ionizing radiation; heating the medium to above the melting point of the irradiated UHMWPE (above about 137° C.) to eliminate the crystalline matter and allow for the recombination/elimination of the residual free radicals; and sterilizing the medical implant with a gas, for example, ethylene oxide or gas plasma.

Heating: One aspect of the present invention discloses a process of increasing the uniformity of the antioxidant following doping in polymeric component of a medical implant during the manufacturing process by heating for a time period depending on the melting temperature of the polymeric material. For example, the preferred temperature is about 137° C. or less. Another aspect of the invention discloses a heating step that can be carried in the air, in an atmosphere, containing oxygen, wherein the oxygen concentration is at least 1%, 2%, 4%, or up to about 22%, or any integer thereabout or therebetween. In another aspect, the invention discloses a heating step that can be carried while the implant is in contact with an inert atmosphere, wherein the inert atmosphere contains gas selected from the group consisting of nitrogen, argon, helium, neon, or the like, or a combination thereof. In another aspect, the invention discloses a heating step that can be carried while the implant is in contact with a non-oxidizing medium, such as an inert fluid medium, wherein the medium contains no more than about 1% oxygen. In another aspect, the invention discloses a heating step that can be carried while the implant is in a vacuum.

In another aspect of this invention, there is described the heating method of implants to reduce increase the uniformity of the antioxidant. The medical device comprising a polymeric raw material, such as UHMWPE, is generally heated to a temperature of about 137° C. or less following the step of doping with the antioxidant. The medical device is kept heated in the inert medium until the desired uniformity of the antioxidant is reached.

The term "below the melting point" or "below the melt" refers to a temperature below the melting point of a polyethylene, for example, UHMWPE. The term "below the melting point" or "below the melt" refers to a temperature less than 145° C., which may vary depending on the melting temperature of the polyethylene, for example, 145° C., 140° C. or 135° C., which again depends on the properties of the polyethylene being treated, for example, molecular weight averages and ranges, batch variations, etc. The melting temperature is typically measured using a differential scanning calorimeter (DSC) at a heating rate of 10° C. per minute. The peak melting temperature thus measured is referred to as melting point and occurs, for example, at approximately 137° C. for some grades of UHMWPE. It may be desirable to conduct a melting study on the starting polyethylene material in order to determine the melting temperature and to decide upon an irradiation and annealing temperature.

The term "annealing" refers to heating the polymer below its peak melting point. Annealing time can be at least 1 minute to several weeks long. In one aspect the annealing time is about 4 hours to about 48 hours, preferably 24 to 48 hours and more preferably about 24 hours. "Annealing temperature" refers to the thermal condition for annealing in accordance with the invention.

The term "annealing" also refers to heating antioxidant-doped or antioxidant-emulsion-doped polymeric material or UHMEPE-based material under a liquid or gaseous environment under various temperature and pressure conditions. For example, annealing can be carried out in water or antioxidant-emulsion or antioxidant-solution at temperature between room temperature boiling point of water or the hydrophilic component of the emulsion under atmospheric pressure, or under pressure at a temperature above 100° C. and below the melting point of the polymeric material. Annealing of antioxidant-doped-polymeric materials or antioxidant-doped-cross-linked polymeric materials prior to machining also can be carried out at a temperature above the melting point of the polymeric material, for example, at 150° C., 160° C., 170° C., 180° C., 190° C., 200° C., or higher.

Annealing time in liquid or gaseous environment can be carried out for a time period between about 1 minute and about 30 days, preferably between about 1 hour and about 3 days, more preferably between about 10 hours and about 3 days, and even more preferably for about 24 hours.

Annealing of polymeric material or UHMWPE-based material also can be done in a fluid under pressure at a temperature above 100° C. and below the melting point of the polymeric material. Annealing of polymeric material or UHMWPE-based material prior to machining also can be carried out at a temperature above the melting point of the material, for example, at 150° C., 160° C., 170° C., 180° C., 190° C., 200° C., or higher.

The term "fluid" refers to liquids and gases, including mineral oil, water, alcohols, and dimethyl sulfoxide, steam, vapor, aerosols, emulsions, solutions, mixtures, and the like.

The term "contacted" includes physical proximity with or touching such that the sensitizing agent can perform its intended function. Preferably, a polyethylene composition or pre-form is sufficiently contacted such that it is soaked in the sensitizing agent, which ensures that the contact is sufficient. Soaking is defined as placing the sample in a specific environment for a sufficient period of time at an appropriate temperature, for example, soaking the sample in a solution of an antioxidant. The environment is heated to a temperature ranging from room temperature to a temperature below or above the melting point of the material. The contact period ranges from at least about 1 minute to several weeks and the duration depending on the temperature of the environment.

The term "non-oxidizing" refers to a state of polymeric material having an oxidation index (A. U.) of less than about 0.5 following aging polymeric materials for 5 weeks in air at 80° C. oven. Thus, a non-oxidizing cross-linked polymeric material generally shows an oxidation index (A. U.) of less than about 0.5 after the aging period.

The term "doping" refers to a process well known in the art (see, for example, U.S. Pat. Nos. 6,448,315 and 5,827,904) and as described above. In this connection, doping generally refers to contacting a polymeric material or a medical implant containing polymeric material with an antioxidant under certain conditions, as set forth herein, for example, doping UHMWPE with an antioxidant under supercritical conditions.

More specifically, consolidated polymeric material can be doped with an antioxidant by soaking the material in a solution of the antioxidant. This allows the antioxidant to diffuse into the polymer. For instance, the material can be soaked in 100% antioxidant. The material also can be soaked in an antioxidant solution where a carrier solvent can be used to dilute the antioxidant concentration. To increase the depth of diffusion of the antioxidant, the material can be doped for longer durations, at higher temperatures, at higher pressures, and/or in presence of a supercritical fluid.

The doping process can involve soaking of a polymeric material, medical implant or device with an antioxidant, such as vitamin E, for about an hour up to several days, preferably for at least about one hour to 24 hours, more preferably for at least one hour to 16 hours. The antioxidant can be heated to room temperature or up to about 160° C. and the doping can be carried out at room temperature or up to about 160° C. Preferably, the antioxidant can be heated to 105° C. or 110° C. and the doping is carried out at 105° C. or 110° C.

The doping step can be followed by a heating step in air or in anoxic environment to improve the uniformity of the antioxidant within the polymeric material, medical implant or device. The heating may be carried out above or below or at the peak melting point. For example, doping of polymeric materials prior to machining can be carried out at a temperature above the melting point of the polymeric material, for example, at 150° C., 160° C., 170° C., 180° C., 190° C., 200° C., or higher.

In another aspect of the invention the medical device is cleaned before packaging and sterilization.

The invention is further described by the following examples, which do not limit the invention in any manner.

EXAMPLES

Vitamin E

Vitamin E (Acros™ 99% D-α-Tocopherol, Fisher Brand), was used in the experiments described herein, unless otherwise specified. The vitamin E used is very light yellow in color and is a viscous fluid at room temperature. Its melting point is 2-3° C.

Example 1

Consolidation of UHMWPE Resin Mixed with Vitamin E

Vitamin E was dissolved in ethanol to create a solution with 10% (w/v) vitamin E concentration. The vitamin E-ethanol solution was then dry-blended with GUR 1050 ultra-high molecular weight polyethylene (UHMWPE) resin. Two batches were prepared: one with vitamin E concentration of 0.1% (w/v) and the other with 0.3% (w/v). The vitamin E concentrations were measured after evaporation of ethanol. Both batches were than consolidated on a Carver laboratory bench pressed at a temperature of 230° C. in air. The consolidated blocks were discolored. The 0.1% (w/v) solution appeared dark yellow and the 0.3% (w/v) solution had a brown color. The discoloration was uniform throughout the consolidated UHMWPE blocks.

The discoloration was thought to be the result of the degradation of vitamin E when heated in presence of oxygen.

Example 2

Discoloration of Vitamin E when Exposed to Heat in Air or in Vacuum

An experiment was carried out to determine if the vitamin E discoloration is due to exposure to air at elevated temperatures and if the discoloration could be avoided by heating vitamin E under vacuum.

One drop of vitamin E solution, as described herein, was placed on a laboratory glass slide. The glass slide was then heated in an air convection oven to 180° C. for 1 hour in air. The vitamin E changed its color to a dark brown. The discoloration was most probably due to the degradation of the vitamin E.

One drop of vitamin E was placed on a laboratory glass slide. The glass slide was then heated in a vacuum oven to 180° C. for 1 hour under vacuum. In contrast to heating in air, vitamin E showed no discernible color change following heating in vacuum. Therefore, in the absence of air or oxygen, heat treatment of vitamin E results in no discernable color change.

Example 3

Consolidation of UHMWPE/Vitamin E in Anoxic Environment

Vitamin E is dissolved in ethanol to create a solution. GUR1050 polyethylene resin is degassed either in vacuum or is kept in an anoxic environment to substantially remove the dissolved oxygen. The vitamin E-ethanol solution is then dry-blended with GUR1050 polyethylene resin. Two batches are prepared, one with degassed GUR1050 and the other with the as-received GUR1050 polyethylene resin. The dry-blended mixtures are then separately consolidated on a Carver laboratory bench press. Consolidation can be carried out in an anoxic environment to minimize the discoloration of the consolidated stock.

Example 4

Pin-on-Disk (POD) Wear Test of Pins Treated with 0.1% and 0.3% Vitamin E

An experiment was carried out to determine the effects of vitamin E on crosslinking efficiency of UHMWPE. Vitamin E (α-tocopherol) was mixed with GUR1050 UHMWPE powder, in two concentrations, for example, 0.1% and 0.3% weight/volume, and consolidated. The consolidation of UHMWPE into blocks was achieved by compression molding. One additional consolidation was carried out without vitamin E additive, to use as a control. The three consolidated blocks were machined into halves and one half of each was packaged in vacuum and irradiated to 100 kGy with gamma radiation (Steris, Northborough, Mass.).

Cylindrical pins, 9 mm in diameter and 13 mm in length, were cut out of the irradiated blocks. The pins were first subjected to accelerated aging at 80° C. for 5 weeks in air and subsequently tested on a bi-directional pin-on-disk (POD). The POD test was run for a total of 2 million cycles with gravimetric assessment of wear at every 0.5 million cycles. The test was run at a frequency of 2 Hz with bovine serum, as a lubricant.

The typical wear rate of UHMWPE with no radiation history and no vitamin E is around 8.0 milligram per million cycles. The wear rates for the 100 kGy irradiated vitamin E added pins were 2.10±0.17 and 5.01±0.76 milligram per million cycles for the 0.1% and 0.3% vitamin E concentrations, respectively. The reduction in wear resistance is less with higher vitamin E content.

By increasing vitamin E content, the radiation induced long-term oxidative instability of polyethylene can be decreased. In other words, improved resistance to post-irradiation oxidation of UHMWPE can be achieved by blending with vitamin E. However, the crosslink density of UHMWPE, achieved by a high irradiation dose, decreases with increasing concentration of vitamin E content in the mixture.

Example 5

Diffusion of Vitamin E into Consolidated Polyethylene

A drop of vitamin E was placed on a machined surface of consolidated GUR1050 UHMWPE in air. In six hours, the vitamin E drop was no longer visible on that machined surface, indicating that it had diffused into the polyethylene.

Example 6

Diffusion of Vitamin E into Irradiated Polyethylene

Compression molded GUR1050 UHMWPE (Perplas, Lanchashire, UK) was irradiated using gamma radiation at a dose level of 100 kGy. Cylindrical pins (n=10) of 9 mm diameter and 13 mm height were machined from the irradiated stock. One of the basal surfaces of five of the pins (n=5) were wetted with vitamin E. The other five pins served as control samples. The two groups of pins were left in air at room temperature for 16 hours. They were then placed in a convection oven at 80° C. in air for accelerated aging.

The aged pins were removed from the oven after five weeks to determine the extent of oxidation. The pins were first cut in half along the axis of the cylinder. One of the cut surfaces was then microtomed (150-200 micrometer) and a BioRad UMA 500 infra-red microscope was used to collect infra-red spectrum as a function of distance away from the edge corresponding to one of the basal surfaces of the cylinder. In the case of the vitamin E treated pins, the oxidation level was quantified from the basal surface that was wetted with vitamin E.

Oxidation index was calculated by normalizing the area under the carbonyl vibration ($1740$ $cm^{-1}$) to that under the methylene vibration at $1370$ $cm^{-1}$, after subtracting the corresponding baselines.

The oxidation levels were substantially reduced by the application of vitamin E onto the surface of irradiated polyethylene. Therefore, this method can be used to improve the long-term oxidative stability of irradiated polyethylene, for example, in medical devices containing polymeric material.

Example 7

Diffusion of Vitamin E into Polyethylene Followed by Irradiation

Compression molded GUR1050 UHMWPE (Perplas, Lanchashire, UK) was machined into cubes (n=4) of 19 mm a side. The surfaces of two cubes were wetted with vitamin E and left at room temperature for 16 hours. Two other cubes were left without addition of vitamin E. One cube of each group with and without vitamin E were packaged in an anoxic environment (for example, about 2% oxygen) and the remaining five cubes of each group were packaged in air. The cubes were irradiated using gamma radiation at a dose level of 100 kGy in their respective packaging.

The irradiated cubes were removed from the packages and placed in an oven at 80° C. in the air for accelerated aging.

The aged cubes were removed from the oven after five weeks to determine the extent of oxidation. The cubes were first cut into halves. One of the cut surfaces was then microtomed (150-200 micrometer) and a BioRad UMA 500 infra-red microscope was used to collect infra-red spectrum as a function of distance away from one of the edges.

Oxidation index was calculated by normalizing the area under the carbonyl vibration ($1740$ $cm^{-1}$) to that under the methylene vibration at $1370$ $cm^{-1}$, after subtracting the corresponding baselines.

The oxidation levels were substantially reduced by the application of vitamin E onto the surface of polyethylene prior to irradiation in air or anoxic environment. Therefore, this method can be used to improve the long-term oxidative stability of polyethylene that may subsequently be irradiated to sterilization and/or crosslinking polymeric material, for example, medical devices containing polymeric material.

Example 8

Fabrication of a Highly Cross-Linked Medical Device

A tibial knee insert is machined from compression molded GUR1050 UHMWPE. The insert is then soaked in 100% vitamin E or a solution of vitamin E. The diffusion of vitamin E into the insert may be accelerated by increasing temperature and/or pressure, which can be carried out either in air or inert or anoxic environment. After reaching desired level of vitamin E diffusion, the insert is packaged either in air or inert or anoxic environment. The packaged insert is then irradiated to 100 kGy dose. The irradiation serves two purposes: (1) crosslinks the polyethylene and improves wear resistance and (2) sterilizes the implant.

In this example the polyethylene implant can be any polyethylene medical device including those with abutting interfaces to other materials, such as metals. An example of this is non-modular, metal-backed, polyethylene components used in total joint arthroplasty.

Example 9

Diffusion of Vitamin E in Polyethylene

An experiment was carried out to investigate the diffusion of synthetic vitamin E (DL-α-tocopherol) into UHMWPE. Consolidated GUR 1050 UHMWPE (Perplas Ltd., Lancashire, UK) was machined into 2 cm cubes. The cubes were immersed in α-tocopherol (Fisher Scientific, Houston, Tex.) for doping. Doping was carried out in an oven with a nitrogen purge. Cubes were doped at 25° C., 100° C., 120° C., or 130° C. for 16 hours under 0.5-0.6 atm nitrogen pressure, which was applied by first purging the oven with nitrogen, then applying vacuum, and then adjusting the amount of nitrogen (for all except 25° C., which was performed in air at ambient pressure). After doping, the samples were rinsed with ethanol to remove excess α-tocopherol from surfaces of the cubes. The extent of α-tocopherol diffusion into polyethylene was quantified by using infrared microscopy and measuring a characteristic absorbance of α-tocopherol as a function of depth away from a free surface.

The cubes that were doped with α-tocopherol were machined to halves and sectioned (about 100 μm thin sections) using an LKB Sledge Microtome (Sweden). The thin sections were analyzed using a BioRad UMA 500 infrared microscope (Natick, Mass.). Infrared spectra were collected with an aperture size of 50×50 μm as a function of depth away from one of the edges that coincided with the free surface of the cube. The spectra were analyzed by quantifying the absorbance, which is typically generated by vitamin E, namely the absorbance between 1226 and 1275 $cm^{-1}$ wave numbers. The area under the absorbance was integrated and normalized to the area under the reference absorbance peak, located between 1850 and 1985 $cm^{-1}$. The integration of both the vitamin E absorbance and the reference absorbance excluded the respective baselines. The normalized value is referred to as vitamin E index.

FIG. 1 demonstrates the diffusion profiles of polyethylene cubes that were doped at four different temperatures (25° C., 100° C., 120° C. and 130° C.). Depth of α-tocopherol diffusion in polyethylene increased with temperature from 400 μm at 25° C. to 3 mm at 130° C. under ambient pressure.

The diffusion depth and uniformity of the antioxidant, in this example of vitamin E, can be varied by varying the doping temperature.

Example 10

Artificial Aging of UHMWPE with and without Vitamin E

An experiment was performed to investigate the effect of vitamin E on the thermo-oxidative stability of irradiated UHMWPE. Two identical cylindrical pins (9 mm in diameter and 13 mm in height) were machined out of a UHMWPE block that was irradiated to 100 kGy with gamma radiation. One base of one of the cylindrical pins was coated with natural vitamin E (DL-α-tocopherol) and the other pin was left clean. Both pins were then subjected to accelerated aging in an oven at 80° C. in air for 5 weeks. Subsequent to aging, the pins were microtomed to prepare a 200 μm thin section perpendicular to both of the cylindrical bases. Microtomed sections (200 μm each) were then analyzed with a BioRad UMA500 infra-red microscope. Infra-red spectra were collected, as a function of depth away from the edge of the microtomed section, which corresponded to the vitamin E exposed cylindrical base. The spectra were analyzed by quantifying the carbonyl absorbance between 1680 and 1780 $cm^{-1}$ wave numbers. The area under the absorbance was integrated and normalized to the area under the reference absorbance peak located between 1330 and 1390 $cm^{-1}$. The integration of both the carbonyl absorbance and the reference absorbance excluded the respective baselines. The normalized value is referred to as oxidation index.

The clean UHMWPE pin sample showed about six times higher oxidation index than that of the vitamin E treated pin.

Example 11

Improved Oxidation Resistance with Vitamin E Doping

Compression molded GUR 1050 UHMWPE blocks (Perplas Ltd., Lancashire, UK) (3 inches in diameter) were gamma-irradiated in vacuum to a dose of 111 kGy (Steris Isomedix, Northborough, Mass.). Irradiated blocks were machined into half-cubes of dimensions about 2 cm×2 cm×1 cm.

Four groups of the half-cubes were soaked in α-Tocopherol (α-D,L-T, Fischer Scientific, Houston, Tex.) for doping. The half-cubes of the Group RT1 were soaked at room temperature for one hour. The half-cubes of the Group RT16 were soaked at room temperature for 16 hour. The half-cubes of the Group 100C1 were soaked at 100° C. for one hour. The half-cubes of the Group 100C16 were soaked at 100° C. for 16 hours. There were a total 3 half-cubes in each group. In addition, three groups of thermal controls were prepared with three half-cubes in each group. Group TCRT consisted of half-cubes that were machined from one of the irradiated blocks. Group TC100C1 consisted of half-cubes that were heated to 100° C. for one hour in air. Group TC100C16 consisted of half-cubes that were heated to 100° C. for 16 hours in air.

The soaked and thermal control half-cubes described above were then cleaned in a dishwasher. Cleaning was performed by a portable Kenmore dishwasher (Sears Inc, Hoffman Estates, Ill.) on normal cycle with rinse and heat drying. During cleaning, all half-cube test samples were placed in a cylindrical non-elastic polyethylene mesh of 2 inches in diameter and closed at the ends. This ensured that the samples did not move around, but the cleaning medium could get through. Electrasol™ (Reckitt Benckiser Inc., Berkshire, UK) was used as cleaning agent.

Following cleaning, the samples were subject to accelerated aging to determine the effect of tocopherol doping under different conditions on the oxidative stability of the irradiated UHMWPE. Accelerated aging was performed by placing the samples in an oven at 80° C. in air for five weeks.

Subsequent to aging, the half-cubes were cut in halves and microtomed to prepare a 200 μm thin section perpendicular to one of the 2 cm×2 cm surfaces. Microtomed sections (200 μm each) were analyzed with a BioRad UMA500 infra-red microscope. Infra-red spectra were collected, as a function of depth away from the edge of the microtomed section, which corresponded to the surface that was soaked in tocopherol and also exposed to air during aging. The spectra were analyzed by quantifying the carbonyl absorbance between 1680 and 1780 $cm^{-1}$ wave numbers. The area under the absorbance was integrated and normalized to the area under the reference absorbance peak located between 1330 and 1390 $cm^{-1}$. The integration of both the carbonyl absorbance and the reference absorbance excluded the respective baselines. The normalized value is referred to as oxidation index.

Maximum oxidation values of each microtomed sections was calculated and averages of three sections from each Group described above are shown in Table 1. Thermal control for 111 kGy-irradiated, cleaned and aged samples for UHMWPE doped with tocopherol at room temperature showed high levels of oxidation. The average maximum oxidation levels in irradiated, tocopherol doped, cleaned, and aged samples for durations of 1 hour and 16 hours, respectively, were lower than their respective thermal controls that were not doped but had the same thermal history.

Thermal control (Group TC100C1) for 111 kGy irradiated, cleaned and aged samples for UHMWPE doped with tocopherol at 100° C. for 1 hour showed higher levels of oxidation than the corresponding tocopherol doped test samples (Group 100C1). Similarly, thermal control (Group TC100C16) for 111 kGy irradiated, cleaned and aged samples for UHMWPE doped with tocopherol at 100° C. for 16 hours showed higher levels of oxidation than the tocopherol doped test samples (Group 100C16). The oxidation levels of the thermal controls and test samples did not show significant difference between a soak time of 1 hour and 16 hours. The oxidation levels for doped samples at 100° C. were less than those doped at room temperature.

TABLE 1

Maximum oxidation values for cleaned and accelerated aged control and tocopherol doped 111 kGy irradiated UHMWPE

| Sample ID | Average Maximum Oxidation Index |
| --- | --- |
| Group TCRT | 3.68 ± 0.15 |
| Group RT1 | 0.38 ± 0.05 |
| Group RT16 | 0.40 ± 0.03 |
| Group TC100C16 | 0.97 ± 0.04 |
| Group 100C1 | 0.098 ± 0.003 |
| Group TC100C1 | 0.70 ± 0.18 |
| Group 100C16 | 0.080 ± 0.003 |

(RT denotes that doping was done at room temperature).

Figure 2:
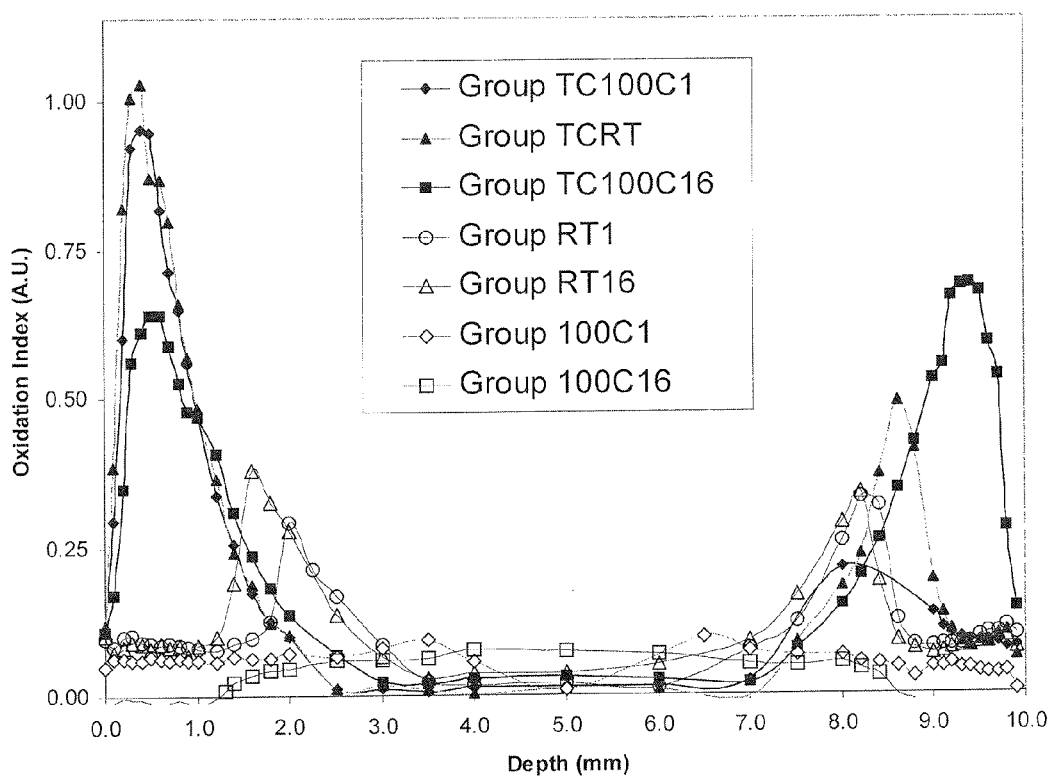
FIG. 2 shows the oxidation index profile as a function of depth into one of the representative aged cubes of seven groups studied (Group TCRT, Group RT1, Group RT16, Group TC100C16, Group 100C1, Group TC100C1, and Group 100C16). All cubes were fabricated from an irradiated polyethylene and four of which were doped with vitamin E under various conditions. Thermal control cubes were not treated with vitamin E. Vitamin E doped cubes show less oxidation at the surface and in the bulk of the samples than their corresponding thermal controls.

FIG. 2 shows the oxidation index profile as a function of depth into one of the representative aged cubes of each group studied (Group TCRT, Group RT1, Group RT16, Group TC100C16, Group 100C1, Group TC100C1, and Group 100C16).

These results show that cleaning by washing and drying did not remove the tocopherol diffused into UHMWPE and tocopherol was able to protect against oxidation of high-dose irradiated UHMWPE under aggressive aging conditions.

Example 12

Ionizing Sterilization of Balloon Catheters

The increased use of drug coatings on balloons and stents precludes the use of ethylene oxide sterilization in many cases. Additionally, improved wear behavior is desired for balloons that are used to inflate metallic stents. Polyethylene balloons are soaked in vitamin E at room temperature and pressure for 16 hours. The balloons are then exposed to ionizing radiation in dose levels ranging from 25 kGy to 100 kGy. The radiation sterilizes the component without affecting the drug, and crosslinks the polyethylene to improve the wear behavior. Oxidation resulting from residual free radicals can be minimized by the presence of the vitamin E.

Example 13

Improved Oxidation Resistance of Packaging Material

Packaging made from polyethylene films is soaked in vitamin E at room temperature and kept under pressure for 16 hours. The packaging is then sterilized by ionizing radiation at doses 25-40 kGy. The packaging is protected from oxidation-induced embrittlement, which can affect both the mechanical integrity and the gas barrier properties of the packaging.

Example 14

Irradiation and Doping of UHMWPE

Cubes (20 mm to a side) were machined from three different bar stocks made out of GUR1050 UHMWPE that are treated as follows: (1) gamma irradiated to 65 kGy, (2) gamma irradiated to 100 kGy, and (3) unirradiated. The cubes were than doped by soaking in vitamin E (DL-α-tocopherol) for 16 hours at room temperature. Two groups of cubes, one machined from the 65 kGy and the other from the 100 kGy irradiated stocks, were packaged following doping with vitamin E and irradiated again with gamma irradiation for sterilization at a dose level of 25-40 kGy. One additional group of cubes, machined from unirradiated stock, was packaged following doping with vitamin E and irradiated again with gamma irradiation for crosslinking and sterilization at a dose level of 125-140 kGy.

Example 15

The Pin-on-Disk (POD) Wear Behavior of Irradiated and Vitamin E Doped UHMWPE Before and after Aging Consolidated GUR 1050 UHMWPE bar stocks were gamma irradiated at 65 kGy and 100 kGy. Cylindrical pins (9 mm in diameter and 13 mm in length) samples for POD wear testing were machined from the irradiated bar stocks. The samples were doped with vitamin E (α-Tocopherol) for 16 hours at room temperature in air. Following doping, the samples were further gamma sterilized at a dose of 27 kGy. These two groups are referred to as α-T-92 and α-T-127 with a total radiation doses of 92 kGy and 127 kGy, respectively.

Half of the cylindrical samples were subjected to accelerated aging at 80° C. in air for five weeks. Both un-aged and aged samples were subjected to POD wear testing. The wear behavior of the pins was tested on a custom-built bi-directional pin-on-disc wear tester at a frequency of 2 Hz by rubbing the pins against an implant-finish cobalt-chrome counterface in a rectangular wear path (Muratoglu et al., *Biomaterials*, 20(16):1463-1470, 1999). The peak contact stress during testing was 6 MPa. Bovine calf serum was used as lubricant and quantified wear gravimetrically at 0.5 million-cycle intervals. Initially, the pins were subjected to 200,000 cycles of POD testing to reach a steady state wear rate independent of diffusion or asperities on the surface. Thereafter, three pins of each group were tested for a total of 2 million cycles. The wear rate was calculated as the linear regression of wear vs. number of cycles from 0.2 to 2 million cycles. The wear rates of doped and aged cross-linked polyethylenes are shown in Table 2.

TABLE 2

The wear rate of doped and aged cross-linked polyethylene.

| Sample ID | Wear rate (milligrams/million-cycles) before aging | Wear rate (milligrams/million-cycles) after aging |
|---|---|---|
| a-T-92 (65 kGy + doping + 27 kGy) | 1.5 ± 0.3 | 1.9 ± 0.5 |
| a-T-127 (100 kGy + doping + 27 kGy) | 0.82 ± 0.2 | 0.91 ± 0.1 |

The wear behavior of the doped samples were comparable before and after aging, indicating that the presence of an antioxidant incorporated by diffusion can protect the irradiated polyethylene from oxidation and thus prevent an increase in wear after aging. Typically the wear rate of a 100 kGy irradiated UHMWPE is around 1 milligrams per million-cycle (Muratoglu et al., *Biomaterials*, 20(16):1463-1470, 1999). Aging of an 105 kGy irradiated UHMWPE can increase its wear rate to above 20 milligram/per cycle (Muratoglu et al. *Clinical Orthopaedics & Related Research*, 417:253-262, 2003).

Example 16

Oxidation Stabilization of Polyether-Block Co-Polyamide Balloons

Balloons fabricated from polyether-block co-polyamide polymer (PeBAX®) are sterilized with either gamma or electron beam after packaging. As there is concern about oxidative embrittlement of these materials due to free radical generation, quenching of the free radicals is imperative to ensure an extended shelf life (for example, a three-year shelf life). These materials cannot be heat-treated following irradiation, given that the highly aligned polymer chains relax when exposed to elevated temperatures, resulting in radial and axial shrinkage.

Polyether-block co-polyamide balloons are soaked in vitamin E, or in a solution of vitamin E and a solvent such as an alcohol. The balloons are packaged, and then subjected to sterilization doses ranging from 25-70 kGy. The higher radiation dose results from double sterilization doses. Sterilization can occur either in air or in a low oxygen atmosphere. The vitamin E minimizes the oxidative behavior of residual free radicals introduced during the sterilization process and also can reduce undesired crosslinking.

Example 17

Oxidation Stabilization of Nylon Balloons

Balloons fabricated from Nylon polymer are sterilized with either gamma or electron beam after packaging. As there is concern about oxidative embrittlement of these materials due to free radical generation, quenching of the free radicals is imperative to ensure a three year shelf life. These materials cannot be heat-treated following irradiation, given that the highly aligned polymer chains relax when exposed to elevated temperatures, resulting in radial and axial shrinkage.

Nylon balloons are soaked in vitamin E, or in a solution of vitamin E and a solvent such as an alcohol. The balloons are packaged, and then subjected to sterilization doses ranging from 25-70 kGy. The higher radiation dose results from double sterilization doses. Sterilization can occur either in air or in a low oxygen atmosphere. The vitamin E minimizes the oxidative behavior of residual free radicals introduced during the sterilization process and also can reduce undesired crosslinking.

Example 18

Oxidation Stabilization of Polyethylene Terephthalate Balloons

Balloons fabricated from polyethylene terephthalate (PET) polymer are sterilized with either gamma or electron beam after packaging. As there is concern about oxidative embrittlement of these materials due to free radical generation, quenching of the free radicals is imperative to ensure an extended shelf life (for example, a three-year shelf life). These materials cannot be heat-treated following irradiation, given that the highly aligned polymer chains relax when exposed to elevated temperatures, resulting in radial and axial shrinkage.

PET balloons are soaked in vitamin E, or in a solution of vitamin E and a solvent such as an alcohol. The balloons are packaged, then subjected to sterilization doses ranging from 25-70 kGy. The higher radiation dose results from double sterilization doses. Sterilization can occur either in air or in a low oxygen atmosphere. The vitamin E minimizes the oxidative behavior of residual free radicals introduced during the sterilization process and also can reduce undesired crosslinking.

Example 19

Oxidation Stabilization of Multi-Component Balloons

Multi-component balloons fabricated from a combination of polymers, including polyethylene, PET, polyether-block co-polyamide, polyvinyl acetate, and nylon, are sterilized with either gamma or electron beam after packaging. As there is concern about oxidative embrittlement of these materials due to free radical generation, quenching of the free radicals is imperative to ensure an extended shelf life (for example, a three-year shelf life). These materials cannot be heat-treated following irradiation, given that the highly aligned polymer chains relax when exposed to elevated temperatures, resulting in radial and axial shrinkage.

These multi-component balloons are soaked in vitamin E, or in a solution of vitamin E and a solvent such as an alcohol. The balloons are packaged, and then subjected to sterilization doses ranging from 25-70 kGy. The higher radiation dose results from double sterilization doses. Sterilization can occur either in air or in a low oxygen atmosphere. The vitamin E minimizes the oxidative behavior of residual free radicals introduced during the sterilization process, and also can reduce undesired crosslinking.

Example 20

Sterilization of Polypropylene Medical Devices

Polypropylene is widely used in the medical industry to produce syringes, vials, and numerous other devices, often through injection molding. Polypropylene is known to exhibit oxidative degradation when it is subjected to ionizing sterilization with gamma or electron beam or gas sterilization with ethylene oxide or gas plasma.

Polypropylene syringes are soaked in vitamin E, or in a solution of vitamin E and a solvent such as an alcohol. The syringes are packaged, and then subjected to sterilization doses ranging from 25-70 kGy. The higher radiation dose results from double sterilization doses. Sterilization can occur either in air or in a low oxygen atmosphere. The vitamin E will minimizes the oxidative behavior of residual free radicals introduced during the sterilization process, and could also reduce undesired crosslinking.

Example 21

Sterilization of Flexible Polyvinyl Chloride Tubing

Flexible polyvinyl chloride (PVC) is used in a variety of medical devices, including tubing. While previously sterilized with ethylene oxide, more manufacturers are using gamma or electron beam to sterilize. Upon exposure to ionizing radiation, these material often darken and yellow, which is believed to be due to oxidation (*Medical Plastics and Biomaterials Magazine*, March, 1996, Douglas W. Luther and Leonard A. Linsky). Yellowing is reduced when antioxidants are compounded into the PVC with a mechanical mixer or extruder.

PVC tubing is soaked in vitamin E, or in a solution of vitamin E and a solvent such as an alcohol. The tubing is then subjected to sterilization doses ranging from 25-70 kGy. The higher radiation dose results from double sterilization doses. Sterilization can occur either in air or in a low oxygen atmosphere. The vitamin E minimizes the oxidative behavior of residual free radicals introduced during the sterilization process, and results in color-stabilized PVC components, as well as improved shelf life.

Example 22

Annealing after Doping

Figure 3:
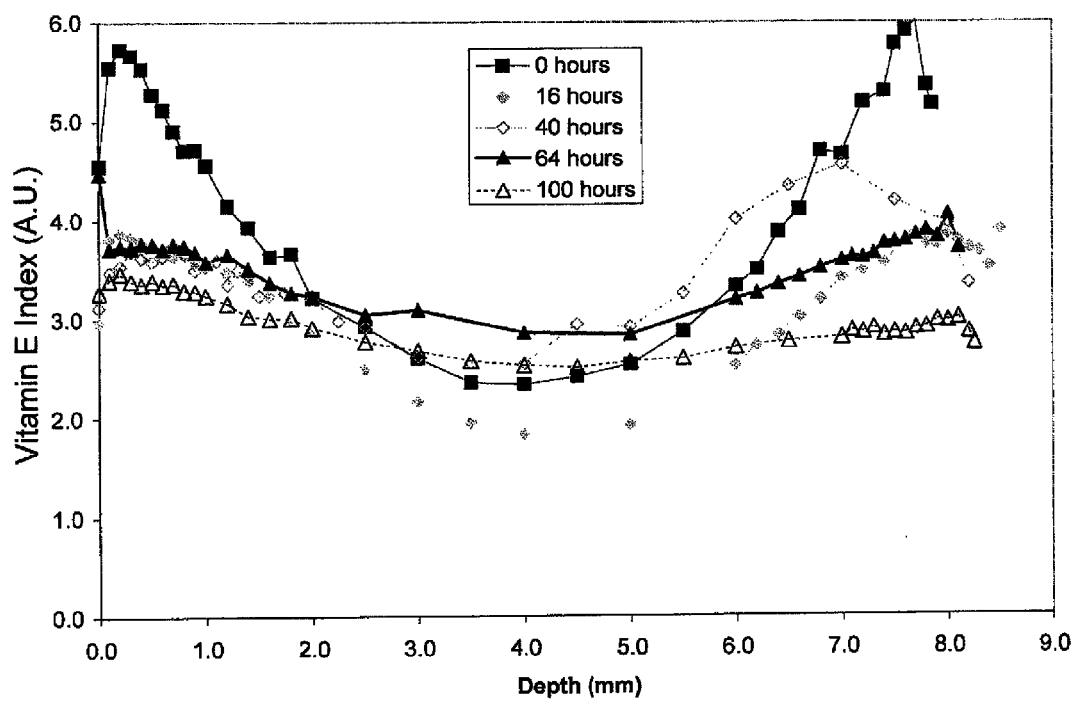
FIG. 3 shows the diffusion profiles for vitamin E through unirradiated UHMWPE doped at 130° C. for 96 hours as a function of subsequent annealing time at 130° C.

Post-doping annealing can be used to achieve a more uniform antioxidant distribution. Unirradiated UHMWPE cubes were doped at 130° C. for 96 hours by soaking in undiluted α-tocopherol. One cube was machined in halves and microtomed. The microtomed sections were analyzed using infra-red microscopy, as described above in Example 9, to measure the vitamin E index as a function of depth away from one of the surfaces that was free during doping. Subsequent to doping, other doped cubes were annealed at 130° C. for increasing periods of time. The doped and annealed cubes were also analyzed using the infrared microscope to determine the changes on the vitamin E index profile as a function of annealing time. FIG. 3 shows the diffusion profiles measured in the doped and also doped and annealed cubes. In the sample that has not been annealed, the surface concentration was much higher than that for the bulk, but the sample that had been annealed for 100 hours at the same temperature showed a nearly uniform profile. Therefore, annealing after doping can be used to increase the uniformity of the antioxidant distribution throughout the host polymer. The temperature and time of annealing can be tailored by carrying out a parametric analysis as described herein.

Example 23

Sequences of Processing UHMWPE

UHMWPE can be doped with antioxidants at various stages, for example, as schematically shown in FIGS. 4 and 5.

Example 24

Post-Doping Annealing in Boiling Water

UHMWPE was irradiated to 100 kGy with gamma irradiation. Six cubes (20 mm to a side) were machined from the irradiated UHMWPE. The cubes were then soaked in vitamin E (α-tocopherol) at various temperatures. Two cubes were soaked in 100° C. vitamin E for 24 hours, two other cubes were soaked in 105° C. vitamin E for 24 hours, and the remaining two cubes were soaked in 110° C. vitamin E for 24 hours. Following the vitamin E doping step, one cube of each temperature group was cut in half and a 200 μm thin section was microtomed. The thin section was then analyzed using a BioRad UMA 500 infra-red microscope as a function of distance away from the edge that corresponded to one of the surfaces of the cube that was exposed to vitamin E during doping. The other cubes of each temperature group were soaked in boiling water for 24 hours. Subsequently, these boiling water soaked cubes were also microtomed and analyzed with the infra-red microscope as described above. The infra-red spectra collected from the thin sections were analyzed to calculate a sensitive vitamin E index (sensVitE), defined as:

sensVitE=(Area under the absorbance peak with limits of 1245 to 1275 $cm^{-1}$) divided by (Area under the absorbance peak with limits of 1850 to 1985 $cm^{-1}$).

The absorbance peak bound by the wave numbers 1245 and 1275 $cm^{-1}$ is a characteristic peak of vitamin E. The intensity of this absorbance peak increases with increasing vitamin E content in UHMWPE.

The depth-profiles of sensVitE for each cube are shown in FIGS. 6A and 6B. FIG. 6A depicts vitamin E profiles obtained in vitamin E doped cubes that were machined from a 100 kGy irradiated UHMWPE (solid marks) and the vitamin E profiles of the doped cubes after annealing in boiling water (hollow marks). Annealing in boiling water improved the penetration depth of the vitamin E into irradiated UHMWPE (see FIG. 6A).

FIG. 6B shows the vitamin E penetration profiles at a higher resolution. Results indicate that the 105° C. 24 hour doped and 24 hour 100° C. exhibited more penetration than the 105° C. 48 hours doped sample, even though both were at an elevated temperature between 100-105° C. for a total of 48 hours.

Example 25

Doping of Irradiated UHMWPE in Vitamin E Emulsion

Two UHMWPE stock materials were irradiated to 100 and 110 kGy with gamma irradiation. Four cubes (20 mm to a side) were machined from the irradiated UHMWPE stock materials. One cube (100 kGy) were then soaked in a mixture of 30% vitamin E (α-tocopherol) and 70% deionized water at 100° C. for 24 hours. The remaining three cubes (110 kGy) were soaked in 100% vitamin E at about 100° C. One cube was removed from the 100% vitamin E bath after 24, 50, and 72 hours of soaking. Following the doping steps, all cubes were cut in half and a 200 μm thin section was microtomed. The thin sections were then analyzed using a BioRad UMA 500 infra-red microscope as a function of distance away from the edge that corresponded to one of the surfaces of the cube that was exposed to vitamin E or vitamin E emulsion during doping. The infra-red spectra collected from the thin sections were analyzed to calculate a sensitive vitamin E index (sensVitE).

The depth-profiles of sensVitE are shown in FIGS. 7A and 7B. FIG. 7A depicts vitamin E profiles obtained from the 24 hour doped cubes. Doping at 100° C. in the vitamin E emulsion resulted in a higher vitamin E surface concentration and a deeper vitamin E penetration than the cube that was doped in 100% vitamin E. FIG. 7B shows the vitamin E profiles of cubes doped for various time periods. Doping at 100° C. in vitamin E emulsion resulted in a diffusion profile equivalent to 72 hours of doping in 100% vitamin E at 100° C. Therefore, doping in an emulsion of vitamin E is more effective than doping in pure vitamin E.

Example 26

Doping of Irradiated UHMWPE Followed by Annealing in Boiling Water or in Boiling NaCl Aqueous Solution UHMWPE stock material was irradiated to 100 kGy with gamma irradiation. Three cubes (20 mm to a side) were machined from the irradiated UHMWPE stock materials. All three cubes were then soaked in 100% vitamin E (α-tocopherol) at 105° C. for 24 hours. One of the cubes was then cooled down to room temperature and soaked in boiling 8 molar aqueous, sodium-chloride solution in a reflux chamber for 24 hours. One of the remaining two cubes was soaked in boiling deionized water in a reflux chamber for 24 hours. The third cube was not treated after the initial vitamin E doping step. All three cubes were then cut in half and a 200 μm thin section was microtomed. The thin sections were then analyzed using a BioRad UMA 500 infra-red microscope as a function of distance away from the edge that corresponded to one of the surfaces of the cube that was exposed to vitamin E or vitamin E emulsion during doping. The infra-red spectra collected from the thin sections were analyzed to calculate a sensitive vitamin E index (sensVitE).

Figure 8:
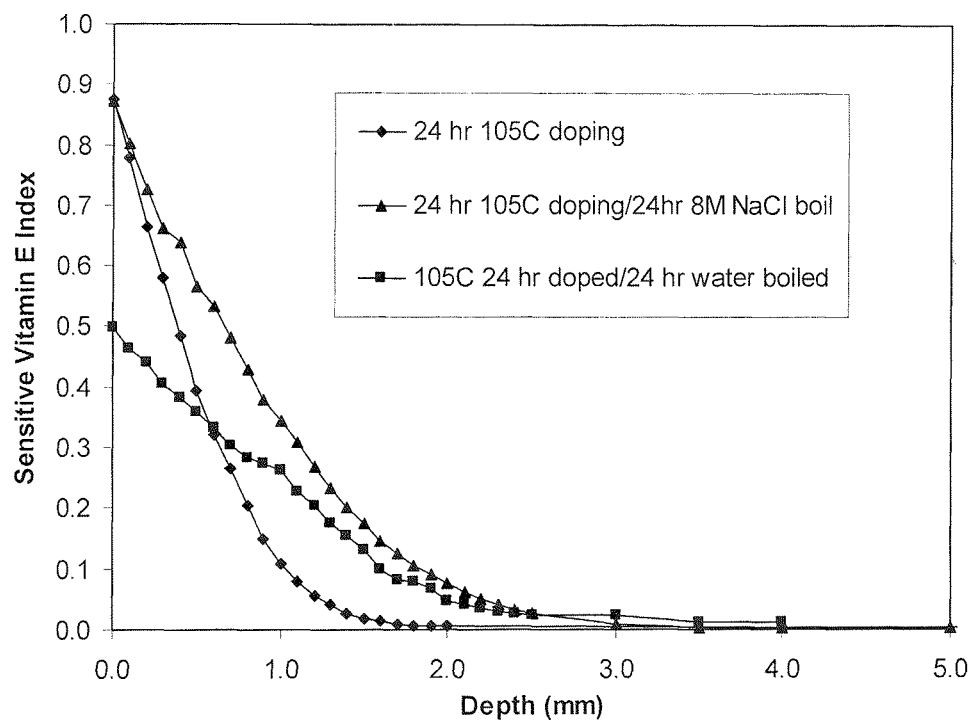
FIG. 8 shows depth-profiles of sensitive vitamin E index (sensVitE) for vitamin E doped UHMWPE cubes and the sensVitE of UHMWPE cubes that were subjected to post-doping-annealing in boiling water and boiling NaCl solution for 24 hours.

The depth-profiles of sensVitE are shown in FIG. 8. The depth of penetration of vitamin E increased with the post-doping annealing in boiling water; same was true when the boiling NaCl solution was used. The surface concentration of vitamin E was with the boiling NaCl solution than it was with boiling water. Annealing of vitamin E doped UHMWPE in boiling water is beneficial in increasing the depth of penetration of vitamin E. Similarly, annealing of vitamin E doped UHMWPE in boiling NaCl aqueous solution is beneficial in increasing the depth of penetration of vitamin E. Annealing of vitamin E doped UHMWPE in boiling NaCl aqueous solution is more beneficial in keeping the surface concentration of vitamin E higher while also increasing the depth of penetration of vitamin E.

It is to be understood that the description, specific examples and data, while indicating exemplary embodiments, are given by way of illustration and are not intended to limit the present invention. Various changes and modifications within the present invention will become apparent to the skilled artisan from the discussion, disclosure and data contained herein, and thus are considered part of the invention.

The invention claimed is:

1. A method of making a hybrid material comprising oxidation-resistant, cross-linked polymeric material containing detectable free radicals, wherein the method comprises:

a) blending polymeric material with an antioxidant;
   b) consolidating the antioxidant blended polymeric material to another piece, thereby forming an interface and an interlocked hybrid material;
   c) irradiating the interlocked hybrid material by ionizing radiation, thereby forming a hybrid material comprising oxidation-resistant, cross-linked polymeric material containing detectable free radicals; and
   d) annealing the oxidation-resistant, cross-linked hybrid material in a liquid environment;
   wherein the method further comprising annealing the oxidation-resistant, cross-linked hybrid material in boiling water, boiling antioxidant-emulsion or boiling antioxidant-solution for about 24 hours.

2. The method of claim 1, wherein the irradiation is carried out at an elevated temperature that is above 50° C. and below the melting point of the polymeric material.

3. The method of claim 1, wherein the irradiation is carried out in an inert atmosphere, wherein the inert atmosphere contains gas selected from the group consisting of nitrogen, argon, helium, and neon, or a combination thereof.

4. The method of claim 1, wherein the irradiation is carried out in a vacuum.

5. The method of claim 1, wherein the radiation dose is between about 25 and about 1000 kGy.

6. The method of claim 1, wherein the radiation dose is about 65 kGy, about 85 kGy, or about 100 kGy.

7. The method of claim 1, wherein the radiation is a gamma irradiation.

8. The method of claim 1, wherein the radiation is an electron beam irradiation.

9. The method of claim 1, wherein the antioxidant is vitamin E.

10. The method of claim 1 further comprising annealing the oxidation-resistant, cross-linked hybrid material at a temperature below the melt of the consolidated and cross-linked polymeric material.

11. The method of claim 1 further comprising annealing the oxidation-resistant, cross-linked hybrid material in boiling water under atmospheric pressure for 100 hours at 100° C.

12. The method of claim 1 further comprising annealing the oxidation-resistant, cross-linked hybrid material in water, antioxidant-emulsion or antioxidant-solution at a temperature between room temperature and boiling point of water, hydrophilic component of the emulsion, or solvent used in the antioxidant solution.

13. The method of claim 1 further comprising annealing the oxidation-resistant, cross-linked hybrid material in water, antioxidant-emulsion or antioxidant-solution at a temperature between about 50° C. and about 100° C.

14. The method of claim 1 further comprising annealing the oxidation-resistant, cross-linked hybrid material in boiling water, boiling antioxidant-emulsion or boiling antioxidant-solution.

15. The method of claim 1 further comprising annealing the oxidation-resistant, cross-linked hybrid material in boiling water, boiling antioxidant-emulsion or boiling antioxidant-solution under atmospheric pressure.

16. The method of claim 1 further comprising annealing the oxidation-resistant, cross-linked hybrid material in water, antioxidant-emulsion or antioxidant-solution for a time period between about 1 minute and about 30 days.

17. The method of claim 1, wherein the irradiation is carried out at an elevated temperature that is above the room temperature and below the melting point of the polymeric material.

18. The method of claim 1, wherein the polymeric material is a polyolefin, a polypropylene, a polyamide, a poly ether ketone, or a mixture thereof.

19. The method of claim 1, wherein the polymeric material is selected from a group consisting of a low-density polyethylene, high-density polyethylene, linear low-density polyethylene, ultra-high molecular weight polyethylene (UHMWPE), or a mixture thereof.

20. The method of claim 1, wherein the polymeric material is polymeric resin powder, polymeric flakes, or polymeric particles, or a mixture thereof.

21. The method of claim 1, wherein the hybrid material comprises medical devices selected from the group consisting of acetabular liner, shoulder glenoid, patellar component, finger joint component, ankle joint component, elbow joint component, wrist joint component, toe joint component, bipolar hip replacements, tibial knee insert, tibial knee inserts with reinforcing metallic and polyethylene posts, intervertebral discs, sutures, tendons, heart valves, stents, vascular grafts.

* * * * *